(12) United States Patent
Katanaev et al.

(10) Patent No.: US 12,104,078 B2
(45) Date of Patent: Oct. 1, 2024

(54) INSECT CORNEAL TYPE NANOCOATINGS

(71) Applicant: Université de Lausanne, Lausanne (CH)

(72) Inventors: Vladimir L. Katanaev, Nyon (CH); Mikhail Kryuchkov, Thônex (CH)

(73) Assignee: Université de Lausanne, Lausanne (CH)

( * ) Notice: Subject to any disclaimer, the term of this patent is extended or adjusted under 35 U.S.C. 154(b) by 892 days.

(21) Appl. No.: 17/057,949

(22) PCT Filed: May 29, 2019

(86) PCT No.: PCT/EP2019/064066
§ 371 (c)(1),
(2) Date: Nov. 23, 2020

(87) PCT Pub. No.: WO2019/229171
PCT Pub. Date: Dec. 5, 2019

(65) Prior Publication Data
US 2021/0207001 A1    Jul. 8, 2021

(30) Foreign Application Priority Data
May 30, 2018    (EP) .................................... 18175103

(51) Int. Cl.
*C09D 189/00*    (2006.01)
*C07K 14/435*    (2006.01)
(Continued)

(52) U.S. Cl.
CPC ...... *C09D 189/00* (2013.01); *C07K 14/43581* (2013.01); *C09D 5/006* (2013.01); *C09D 5/022* (2013.01); *C09D 7/63* (2018.01)

(58) Field of Classification Search
CPC ...... C09D 189/00; C09D 5/006; C09D 5/022; C09D 5/00; C09D 7/63; C07K 14/43581; B82Y 30/00; C03C 17/28
See application file for complete search history.

(56) References Cited

U.S. PATENT DOCUMENTS

| 2,464,759 A * | 3/1949 | Camp ................... C04B 41/478 427/283 |
| 2005/0208558 A1* | 9/2005 | Venter ................. C12Q 1/6888 435/6.16 |

(Continued)

OTHER PUBLICATIONS

Minami et al. "An RNAi Screen for Genes Involved in Nanoscale Protrusion Formation on Corneal Lens in *Drosophila melanogaster*". Zoological Science 33: 583-591 (2016) (Year: 2016).*

(Continued)

*Primary Examiner* — Thomas J. Visone
*Assistant Examiner* — Georgiana C Reglas
(74) *Attorney, Agent, or Firm* — Knobbe, Martens, Olson & Bear, LLP

(57) ABSTRACT

The present invention relates to in vitro nanocoatings based on insect corneal designs and methods for producing such nanocoatings. In particular, the present invention relates to in vitro nanocoatings based on the mixture of the corneal protein retinin, retinin-like protein, or cuticular protein with complementary lipids. Furthermore, the present invention relates to simple methods for producing such nanocoatings from recombinant proteins and commercially available lipids.

14 Claims, 14 Drawing Sheets
Specification includes a Sequence Listing.

(51) Int. Cl.
  *C09D 5/00* (2006.01)
  *C09D 5/02* (2006.01)
  *C09D 7/63* (2018.01)

(56) References Cited

U.S. PATENT DOCUMENTS

| | | | |
|---|---|---|---|
| 2009/0231714 A1 | 9/2009 | Zhao et al. | |
| 2010/0015070 A1* | 1/2010 | Bollschweiler | A61K 8/64 424/59 |
| 2011/0195263 A1* | 8/2011 | Malotky | C08J 3/05 428/480 |
| 2012/0252294 A1* | 10/2012 | Leimer | C04B 41/4807 428/375 |
| 2015/0346398 A1* | 12/2015 | Gorodetsky | G02B 5/26 359/359 |
| 2021/0147686 A1* | 5/2021 | Meyer | C08J 3/05 |

OTHER PUBLICATIONS

Blagodatski A, Sergeev A, Kryuchkov M, and Katanaev VL. Diverse set of Turing nanopatterns coat corneae across insect lineages. PNAS Aug. 11, 2015; 112(34):10750-10755 (Year: 2015).*

Stahl AL, Charlton-Perkins M, Buschbeck EK, Cook TA. The cuticular nature of corneal lenses in *Drosophila melanogaster*. Dev Genes Evol. Jul. 2017;227(4):271-278. (Year: 2017).*

Munoz et al "Fatty acid composition of *Drosophila* photoreceptor light-sensitive microvilli". Biol Res 46: 289-294, 2013 (Year: 2013).*

Fabra et al "Tensile properties and water vapor permeability of sodium caseinate films containing oleic acid-beeswax mixtures" Journal of Food Engineering 85 (2008) 393-400 (Year: 2008).*

Francesco Galeotti et al, "Broadband and Crack-Free Antireflection Coatings by Self-Assembled Moth Eye Patterns", *ACS Applied Materials & Interfaces*, vol. 6, No. 8, Apr. 9, 2014 (Apr. 9, 2014), p. 5827-5834 including Supporting info in 5 pages.

Michail Kryuchkov et al, "Analysis of Micro- and Nano-Structures of the Corneal Surface of *Drosophila* and its Mutants by Atomic Force Microscopy and Optical Diffraction", *PLOS One*, vol. 6, No. 7, Jul. 21, 2011 (Jul. 21, 2011), p. e22237.

Mikhail Kryuchkov et al, "Alternative moth-eye nanostructures: antireflective properties and composition of dimpled corneal nanocoatings in silk-moth ancestors", *Journal of Nanobiotechnology*, vol. 15, No. 1, Sep. 6, 2017 (Sep. 6, 2017).

E. Kim et al, "Characterization of the *Drosophila melanogaster* retinin gene encoding a cornea-specific protein", vol. 17, No. 5, Jan. 1, 2008 (Jan. 1, 2008), p. 537-543.

Yihong Zhou et al, "Distribution of cuticular proteins in different structures of adult Anopheles gambiae", *Insect Biochemistry and Molecular Biology*, vol. 75, Mar. 12, 2016 (Mar. 12, 2016), p. 45-57.

Yifan Si et al, "Superhydrophobic nanocoatings: from materials to fabrications and to applications", *Nanoscale*, vol. 7, No. 14, Jan. 1, 2015 (Jan. 1, 2015), p. 5922-5946.

International Search Report mailed Jul. 31, 2019 for PCT/EP2019/064066 filed May 29, 2019.

* cited by examiner

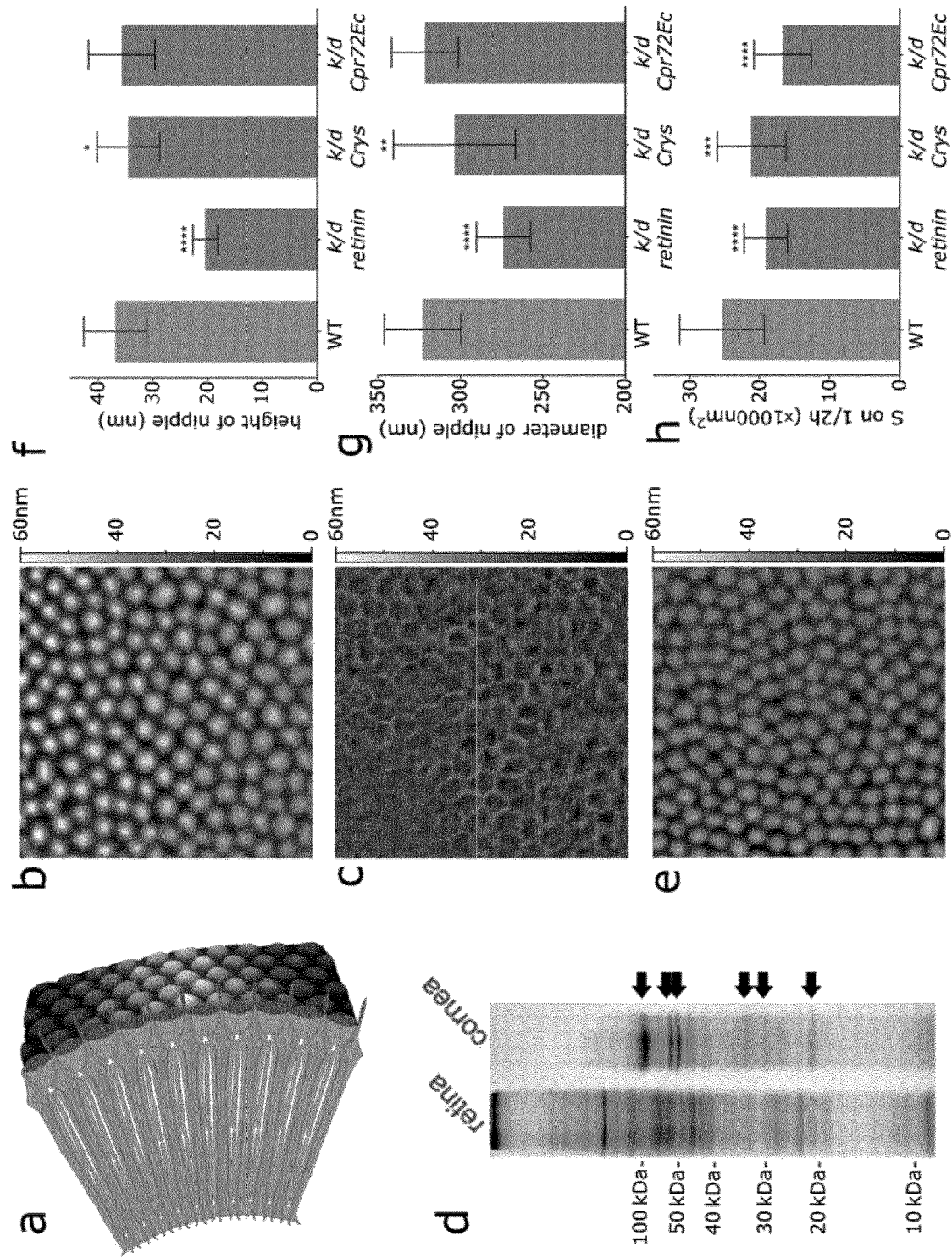
Fig. 2a-h

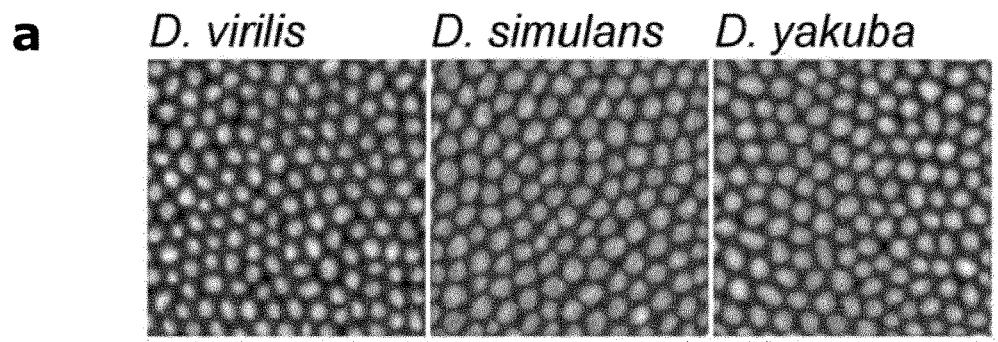
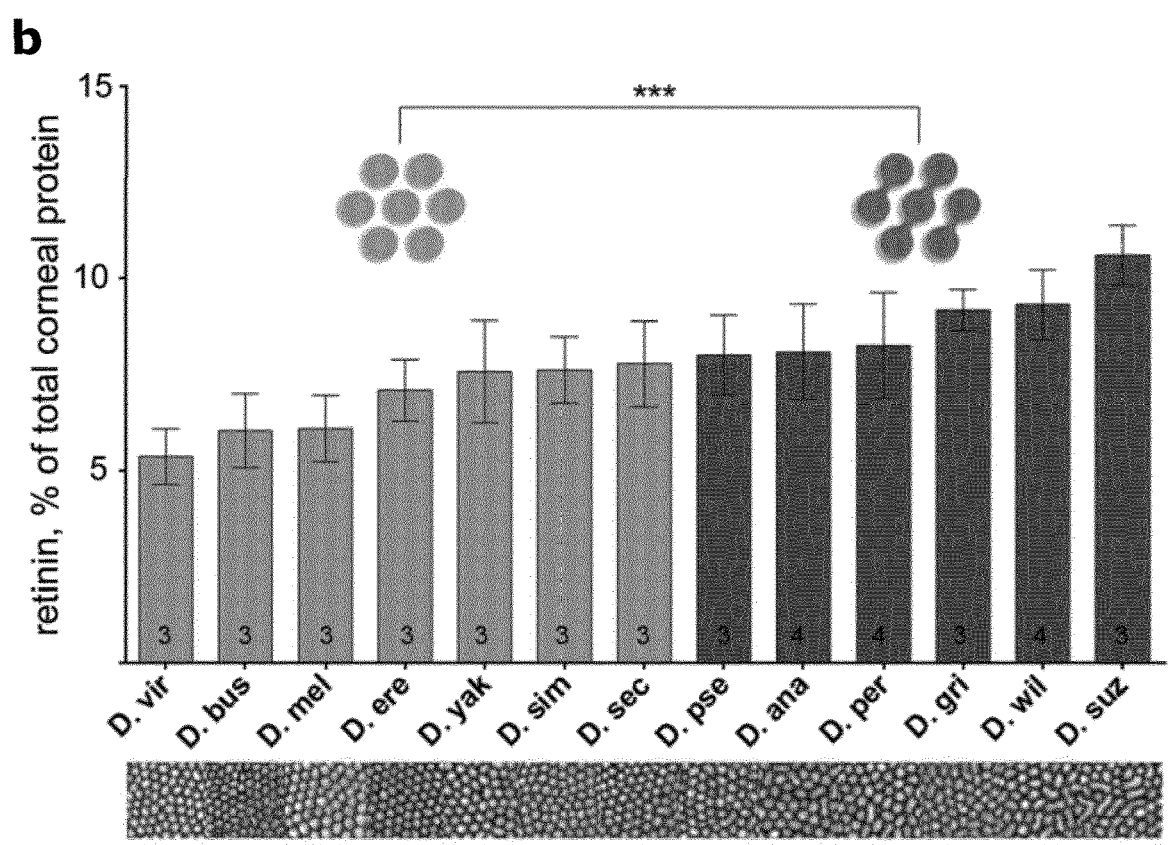
Fig. 3a-b

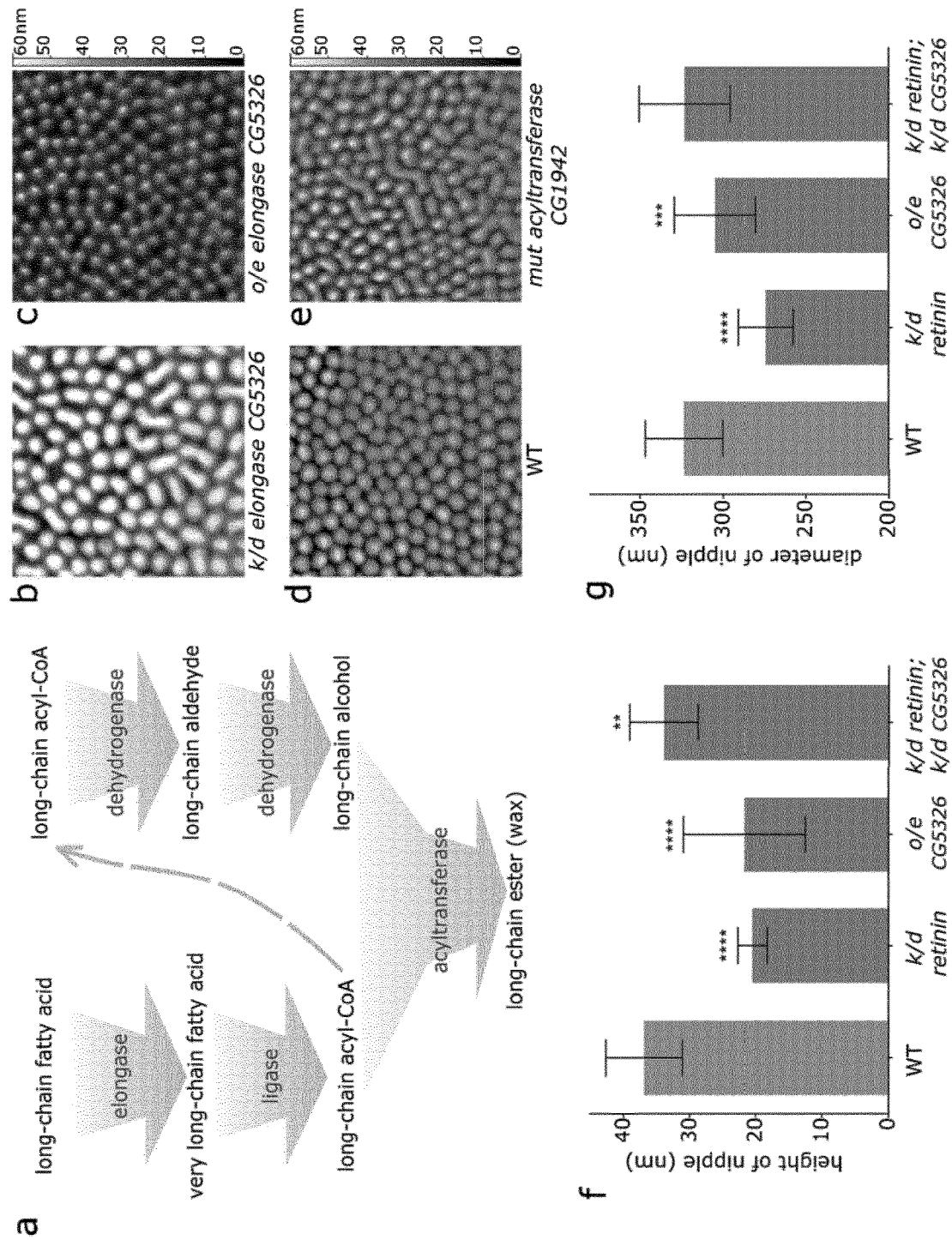
Fig. 4a-g

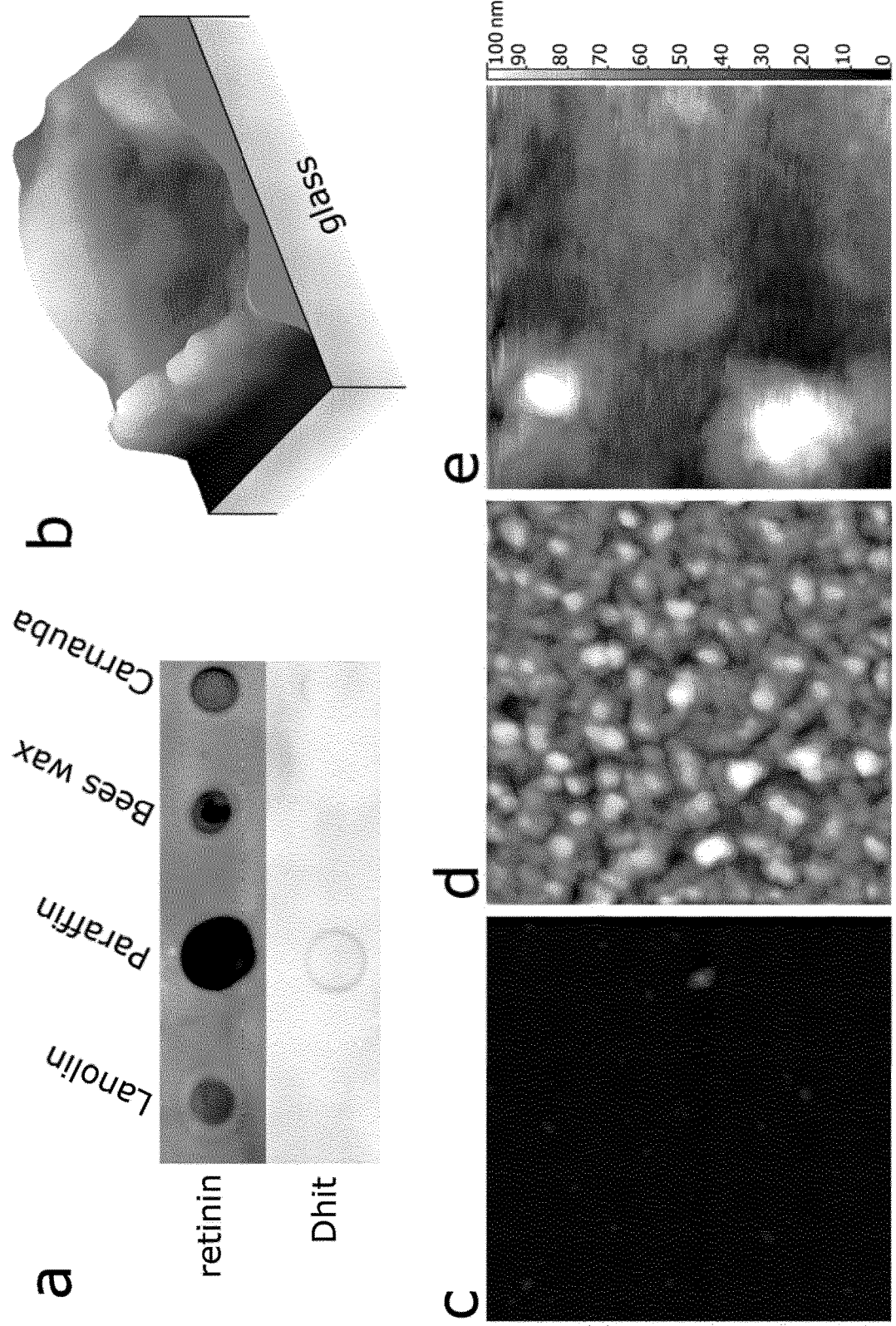
Fig. 5a-e f
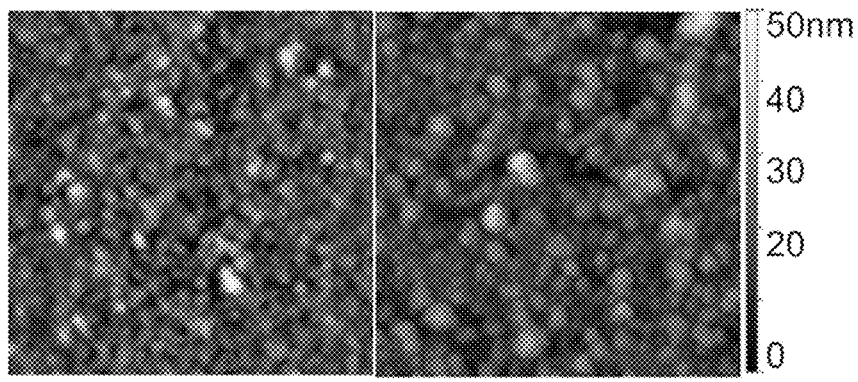
g
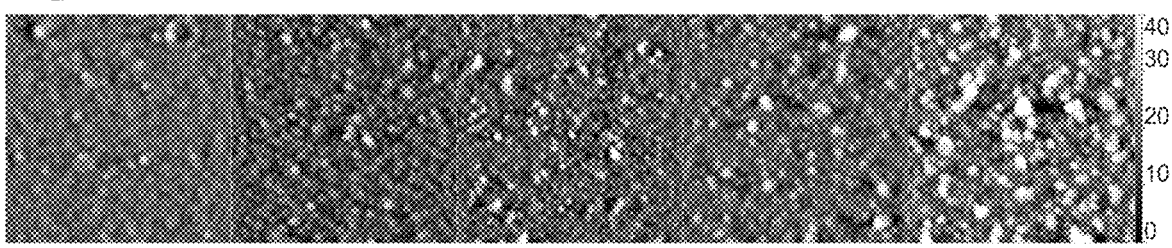
h
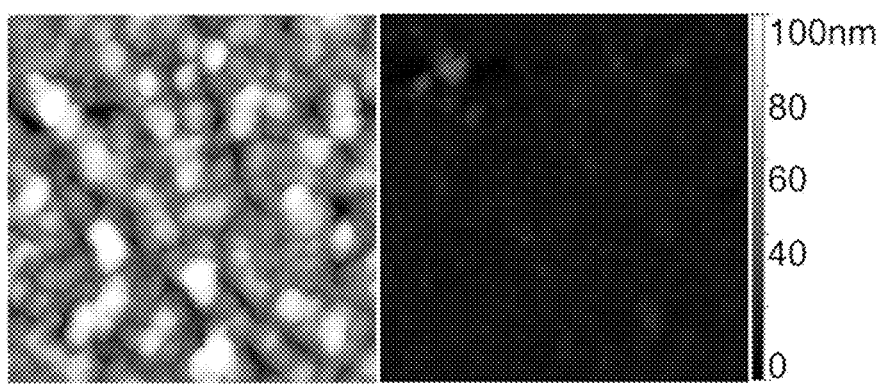
Fig. 5f-h

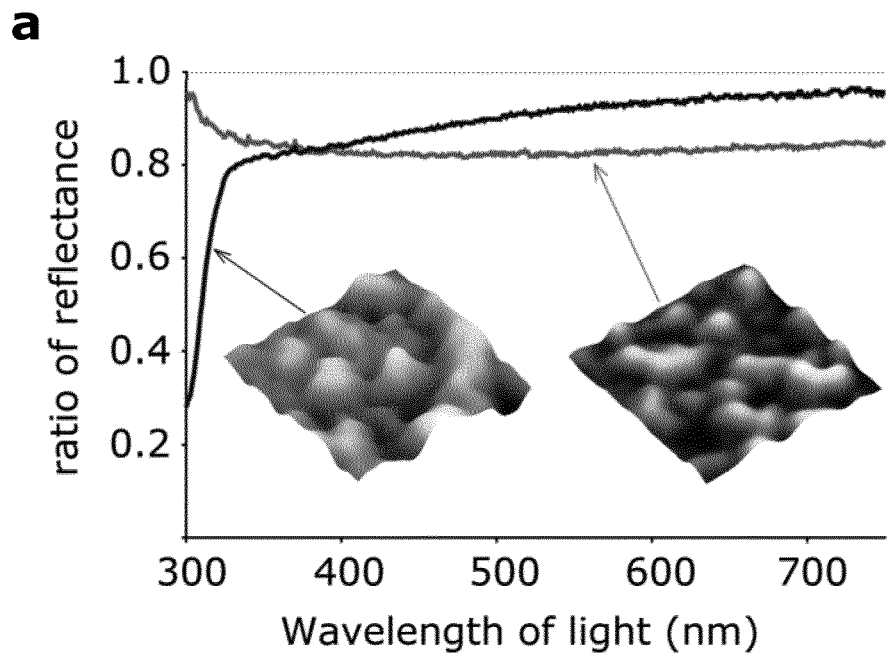
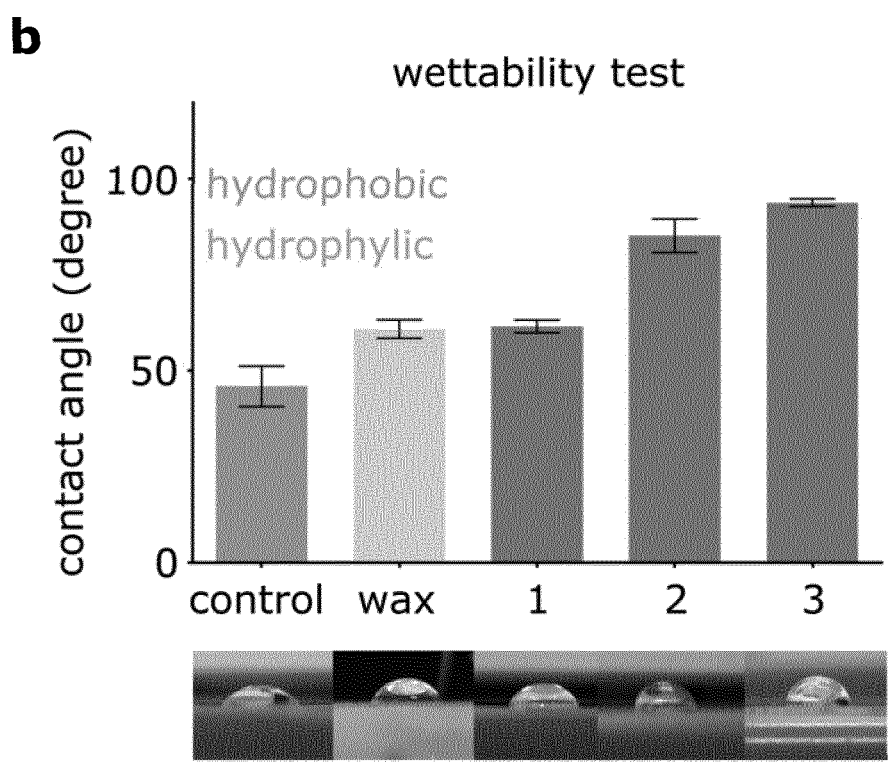
Fig. 6a-b

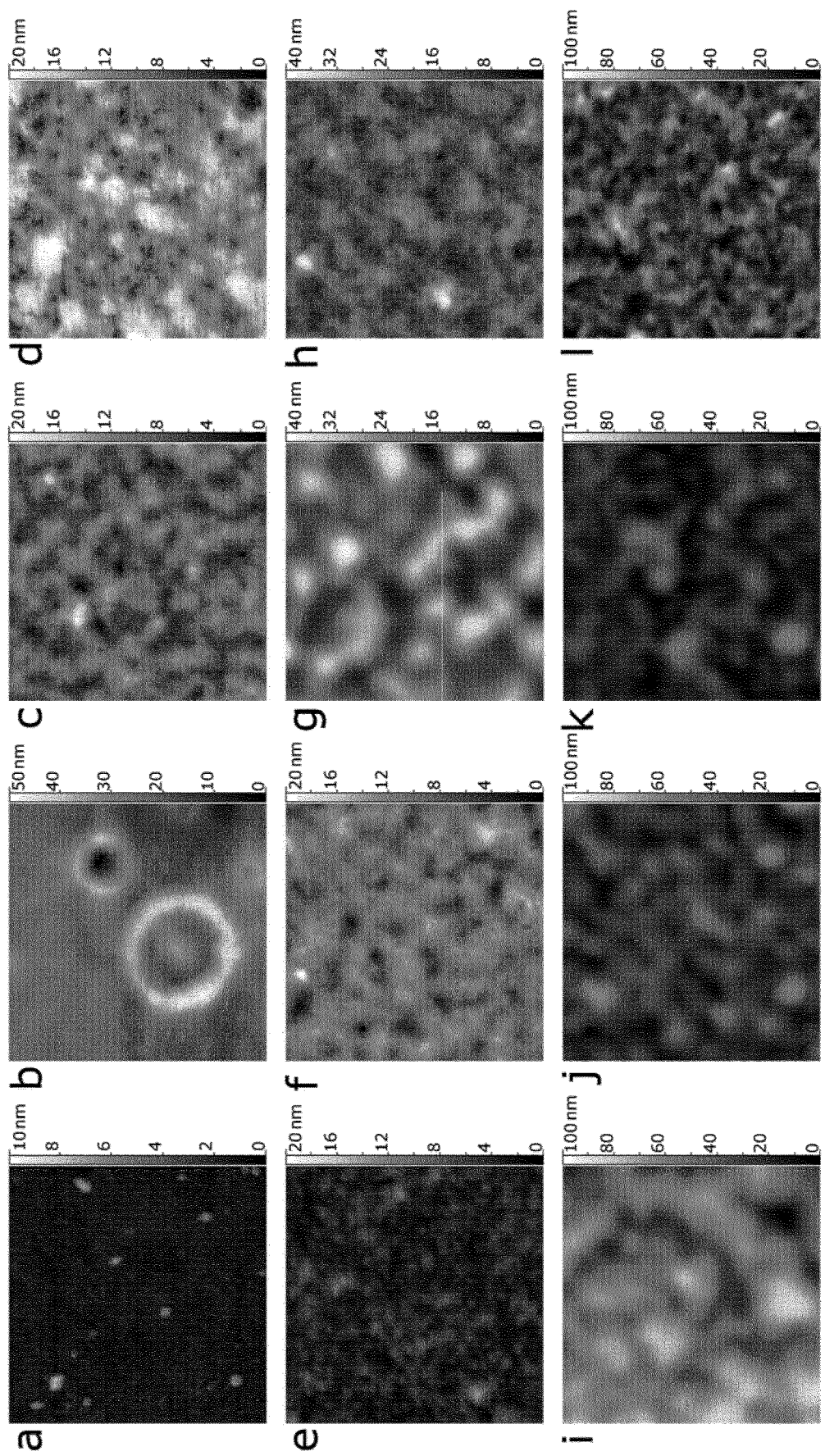
Fig. 7a-l

| materials | | methods | 3D shape | big scale surface (>1m^2) | low process complexity | absence of corrosive/toxic chemicals | easy to modify | bio-degradable | points |
|---|---|---|---|---|---|---|---|---|---|
| Organic polymer | Retinin-like proteins, lipids | Spray/brush | + | + | + | + | + | + | 6 |
| | Pentadecafluorooctanoyl chloride GMA | ATRP | + | + | + | − | − | − | 3 |
| | DFMA, MMA, HEMA, BA | Polymerization, spraying | + | + | − | − | − | − | 2 |
| | Chitosan, CF3(CF2)7SO3Li | Electrostatic reaction, spray | − | + | + | + | + | + | 3 |
| | AAO, PS | Template method | − | − | − | + | + | − | 2 |
| | LDPE, NH4HCO3 | Dip-coating | + | − | − | + | + | − | 2 |
| Organic–inorganic hybrid | ZnO, PS | Hydrothermal reaction, dip-coating | − | − | + | + | − | − | 1 |
| | Aluminum, PP | Microstructure technique/ injection | − | + | − | + | + | − | 2 |
| | PVDF-MWCNT | Spray | + | + | + | + | − | − | 3 |
| | TEOS, PEG | Sol-gel | + | + | − | − | − | + | 3 |
| | PU, MoS2 | Spray | + | + | − | + | + | − | 3 |
| Inorganic: Silica-based | TEOS, OTES | Ultrasound irradiation | − | + | − | + | − | + | 3 |
| | RTV silicone rubber, fluoric NPs | Spray/brush/dip coating | + | + | − | − | + | − | 2 |
| | PDMS, SiO2 NPs, | Spray, calcination | + | + | − | − | − | − | 2 |
| | Fluoro-SNs, Krytox | Coating spread | + | + | + | − | − | − | 3 |
| Carbon-based | Graphene, Nafion | Supramolecular assembly | + | − | + | − | − | − | 2 |
| | Graphene, SH-NPs | Thermal reduction | + | − | − | − | − | − | 1 |
| | CNT | Spray, filtration | + | − | + | − | − | − | 2 |
| | CNT, silicone elastomer | Spray | + | − | + | − | − | − | 2 |
| Metallic | AgCl, AuCl3 | Electroless galvanic reaction | + | − | − | − | − | − | 1 |
| | NiCl, H3BO3, lauryl sodium sulfate | Electrodeposition | + | − | − | − | − | − | 1 |
| | NiCl, CoCl2, C2H8N2, HCl, H3BO3 | Electrodeposition | + | + | + | − | − | − | 1 |
| Metallic oxide | Ag, TiO2 | Plasma deposition | − | − | − | + | − | − | 1 |
| | Al | anodization | + | − | − | + | + | − | 2 |
| | ZnSO4/Al(SO4)3/FeSO4·4H2O | Dip-coating/immerse | − | + | − | − | − | − | 2 |
| | Fe-, Co-, Ni-, Cu-, Ag- oxides, nitrates, etc. | Co-precipitation, immerse | + | + | + | − | − | − | 3 |

Fig. 9

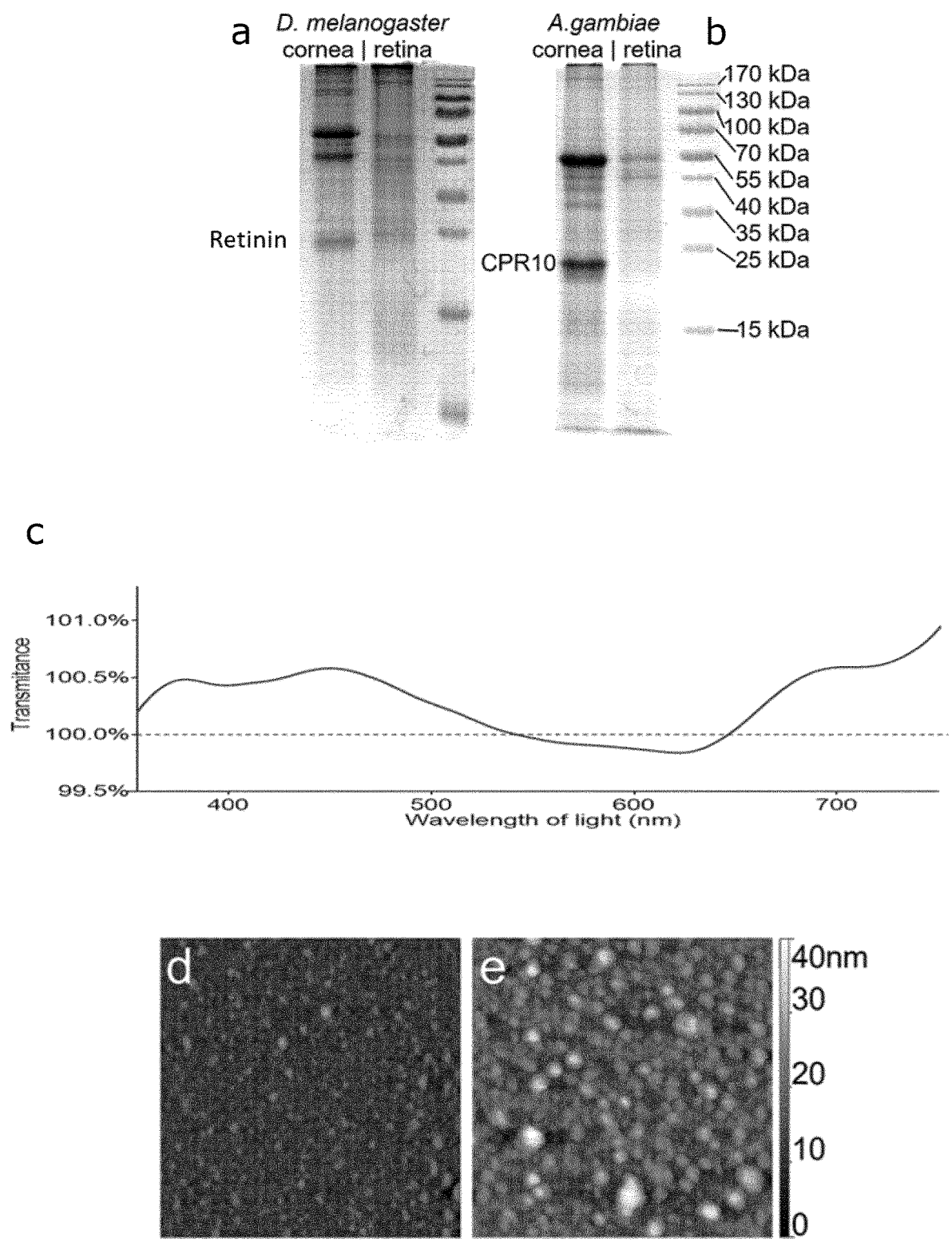
Fig. 10a-e

INSECT CORNEAL TYPE NANOCOATINGS

CROSS REFERENCE TO RELATED APPLICATIONS

This application is a U.S. National Phase application of PCT International Application Number PCT/EP2019/064066, filed on May 29, 2019, designating the United States of America and published in the English language, which is an International Application of and claims the benefit of priority to European Patent Application No. 18175103.3, filed on May 30, 2018. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-PLOUG252-002APC.txt, the date of creation of the ASCII text file is Jun. 3, 2019, and the size of the ASCII text file is 9 KB.

TECHNICAL FIELD OF THE INVENTION

The present invention relates to in vitro nanocoatings with advantageous functionalities based on insect corneal designs and methods for producing such nanocoatings. In particular, the present invention relates to in vitro nanocoatings based on the mixture of the corneal protein retinin or retinin-like protein or cuticular protein with complementary lipids. Furthermore, the present invention relates to simple methods for producing such nanocoatings from recombinant proteins and commercially available lipids.

BACKGROUND OF THE INVENTION

Functional coatings for products of various kinds are utilized extensively in industry to provide products with advantageous properties demanded by the customers. Coatings may be used to alter properties such as adhesion (e.g. non-stick, release), optics (e.g. (anti)-reflectivity, UV-absorbance), catalysis (e.g. self-cleaning), protection (e.g. sealing, anti-corrosion, anti-microbial), magnetism (e.g. media disc, mass transit tickets) or electrical (e.g. conductive, insulating). Thus, the applicability of coatings is widespread and the assortment of coatings have expanded rapidly with the introduction of new techniques suitable for formation of coatings with new and exciting functionalities.

The key to understanding how a coating gives rise to a certain advantageous functional property lies amongst others in the individual components of the coating and their mutual organization on a surface. Many of these coatings are organized on the nanoscale and may as such be termed nanocoatings. With the advancement of nanotechnology, many new tools for characterization of nanostructures have been developed. Consequently, the creation of nanostructured artificial surfaces (i.e. nanocoatings) is today widely used in industry.

Nanocoatings are produced by a large variety of techniques, such as chemical- or physical vapor deposition or other chemical and electrochemical techniques. US 2009/0231714 A1 represents the production of an anti-reflective glass substrate using lithographic techniques. The anti-reflective surface may be coated with a hydrophobic material, such as paraffin wax, to enhance liquid repellence and self-cleaning of the surface.

Common to US 2009/0231714 A1 and other available methods for formation of nanocoatings is that they involve either harsh physical structuring (e.g. lithography, etching etc.) or toxic chemical applications. However, these types of conventional coating protocols are only applicable to highly resistant surface materials. In contrast, some applications require mild conditions, as is the case for e.g. most bio-medical needs or coating of soft matter materials sensitive to harsh treatment. Furthermore, many of the conventional coating techniques are laborious and requires high-tech expensive equipment. These limitations severely hamper the development of biocompatible nanocoatings suitable for use with all types of surfaces, including those not resistant to harsh physical and/or chemical treatment.

Hence, an improved method for formation of in vitro biocompatible nanocoatings would be advantageous. In particular, a more mild method for high-throughput formation of in vitro nanocoatings suitable for use with all types of surfaces would be advantageous.

SUMMARY OF THE INVENTION

The present invention relates to a method for formation of in vitro nanocoatings with advantageous functionalities, such as anti-reflectivity and anti-wettability. Preferably, only biocompatible and mild reagents are used for the formation of the nanocoating, thereby enabling the use of the technology for coating also materials that cannot be treated using conventional harsh physical or chemical treatments. Thus, the proposed method is a versatile tool to enhance also fragile surfaces, such as contact lenses, with new functionalities.

Thus, an object of the present invention relates to the provision of an improved method for formation of in vitro biocompatible nanocoatings, such as a method using mild conditions suitable for application to all types of surfaces, including those not resistant to harsh physical and/or chemical treatment.

In particular, it is an object of the present invention to provide a nanocoating comprising retinin or retinin-like protein or cuticular protein and one or more lipids that may be used to infer a product with one or more properties such as anti-reflectivity and/or anti-wettability.

Thus, one aspect of the invention relates to a method for preparation of a coated surface, said method comprising the following steps:
i. providing a protein solution comprising retinin, retinin-like protein or cuticular protein,
ii. providing an emulsion or suspension comprising one or more lipids,
iii. mixing said protein solution and said emulsion or suspension to provide a liquid mixture,
iv. contacting a surface with said liquid mixture, and
v. drying said surface,
thereby providing a coated surface.

Another aspect of the present invention relates to a coated surface obtainable by mixing
a protein solution comprising retinin, retinin-like protein or cuticular protein, with
an emulsion or suspension comprising one or more lipids
to provide a liquid mixture,
and contacting said surface with said liquid mixture followed by drying said surface.

Yet another aspect of the present invention is to provide a coated surface comprising retinin, retinin-like protein or cuticular protein and one or more lipids.

Still another aspect of the present invention relates to use of a coated surface as described herein to provide a coated product selected from the group consisting of contact lenses, glass-containing surfaces, displays, solar panels, artistic paintings, biological implants, and electric wires.

Figure 1:
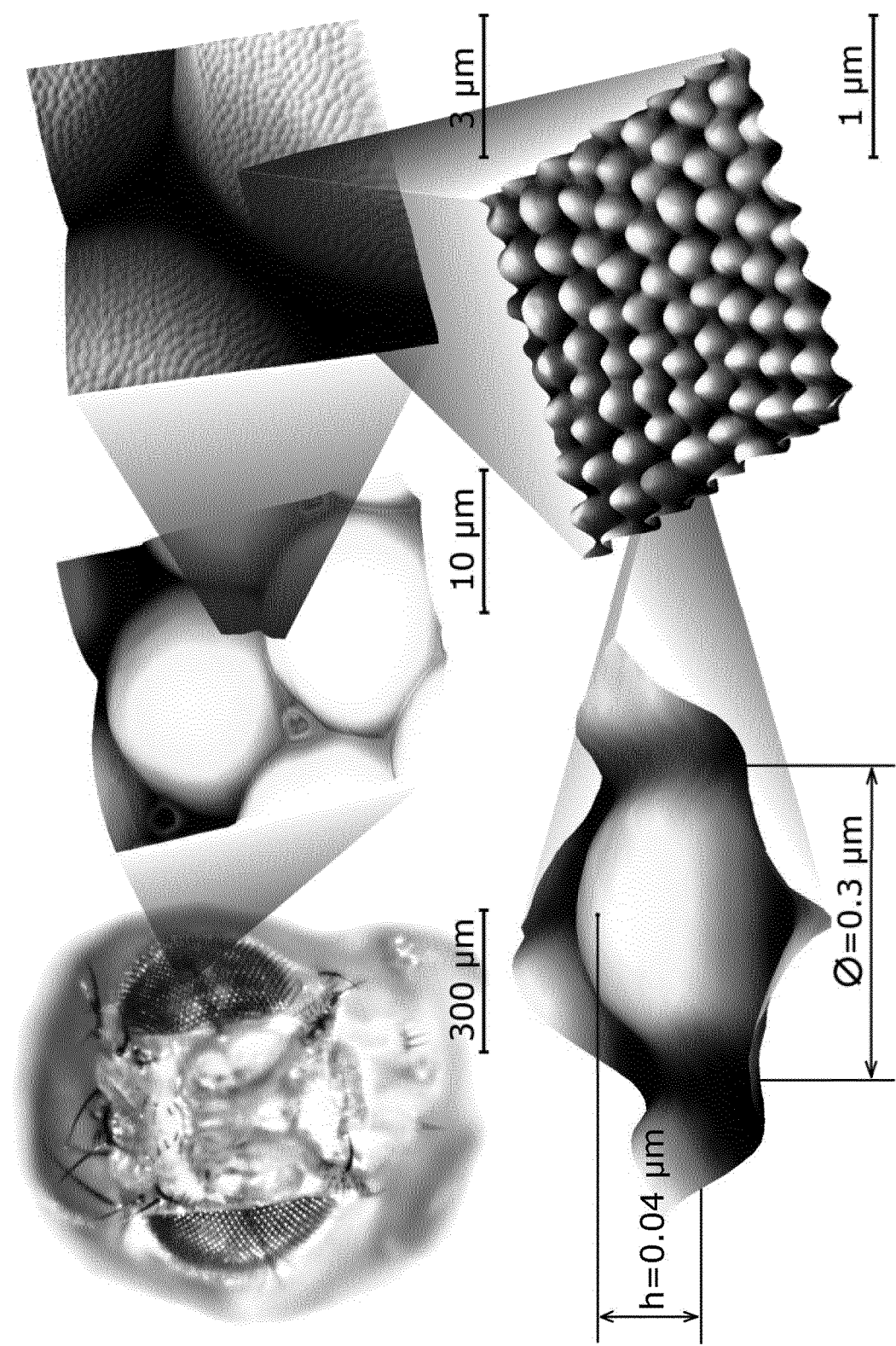
FIG. 1 shows corneal nanocoatings of Drosophila melanogaster. Step-wise increases in magnification are shown, from the macroscopic image of the fruit fly's head to AFM-based resolution of single nipple-type nanostructures coating the individual ommatidial lenses.

(i) Monitoring retinin protein levels in heads of flies of different retinin genotypes: retinin knock-down: UAS-RNAi-retinin; GMR-Gal4; three control lines: Oregon R-C, UAS-RNAi-retinin, and GMR-Gal4; and the three overexpressing lines: UAS-retinin/+; GMR-Gal4/+, UAS-retinin/UAS-retinin; GMR-Gal4/GMR-Gal4 and spa-Gal4/spa-Gal4; UAS-retinin/UAS-retinin; GMR-Gal4/GMR-Gal4.

FIG. 3 shows that retinin expression regulates order and patterning in corneal nanostructures in the Drosophila genus. (a) Analysis of corneal nanocoatings across 14 species of the genus Drosophila reveals two principal types: the D. melanogaster-like nipple-only type seen e.g. D. virilis (upper panel) and the nipple-to-ridge type seen e.g. in D. suzukii (lower panel). (b) The retinin content in corneae of different Drosophila species correlates with the morphological transition from the nipple-only nanostructures (left, light grey) to the nipple-to-ridge nanocoatings (right, dark grey). Numbers of different corneal preparations for SDS-PAGE and densitometry analysis are written on the bars. At least three regions with 300-400 nipple-type nanostructures in each, from at least two different animals were analyzed by AFM for each Drosophila species. Data are presented as mean±sem. Statistical significance of the difference in retinin corneal content between the nipple-only and the nipple-to-ridge groups was assessed by two-way ANOVA; "***" means p-value≤0.001.

(c) Retinins in fruit flies of the Drosophila genus. SDS-PAGE of corneal preparations from different Drosophila species reveals a similar pattern of major proteins, including the ca. 25 kDa protein present in all species and identified by mass-spectrometry as retinin.

FIG. 4 shows that enzymes from pathway of wax synthesis also regulates order and patterning in corneal nanostructures of Drosophila melanogaster. (a) Scheme of the wax synthesis pathway, with necessary enzymes. (b-e) Representative AFM images (3×3 µm) of CG5326 knock-down (k/d) (b), CG5326-overexpressing (o/e) (c), control (d) and CG1942-mutant (mut) (e) corneae. (f, g) Quantification of the height (f) and the diameter (g) of nipple nanostructures for wild type, retinin knock-down, CG5326 overexpression phenotypes, as well as rescue of retinin knock-down phenotype, by downregulation of CG5326 expression. (h) Quantification of the height of nipple nanostructures, wherein the phenotypes (i) retinin overexpression and CG5326 overexpression (third column from the left) and (ii) retinin knock-down and CG5326 overexpression (second column from the right) are also displayed. Data are shown as mean±SD; n=50 different regions were analyzed. Statistical significance of the differences from the control wild-type genotype was assessed by t-test; "" means p-value≤0.01; "*" means p-value≤0.001; "****" means p-value≤0.0001.

FIG. 5 shows that direct interaction between retinin protein and waxes in-vitro form the nanostructured coatings. (a) Direct interaction of the retinin with different waxes shown by dot blot analysis. (b) Cross-section of scratched by AFM tip (on the left side) nanocoating shows the internal organization, with background layer, approximately 20 nm in height. (c-e) Representative AFM images (4×4 µm) of samples, after layering by retinin solution (c), by wax emulsion (e), or by mixture of retinin solution with wax emulsion (d). (f) Representative AFM images (3×3 µm) of nanocoating surfaces obtained by using either paraffin (left) or bees wax (right) in mixture with retinin. (g) Representative AFM images (3×3 µm) of different nanocoatings, obtained by coating with 20 µl of different oil/waxes emulsion (from left to right: olive oil, lanolin wax, paraffin, beeswax, carnauba wax), washed, dried and covered with mixed solution of retinin protein solution in PBS (0.6 mg/ml). (h) Representative AFM images (3×3 µm) of nanocoating surfaces obtained by using carnauba wax in mixture with retinin (left) or in mixture with BSA as a control protein (right).

FIG. 6 shows functionality of the artificial nanocoatings. (a) Ratio of the reflection spectra (from 300 to 750 nm) measured for the different surfaces of artificial nanocoatings and control sample (glass). The spotted line shows the ratio of 1.0 (no reflection difference with control) across the spectrum. (b) The contact angles for different samples: controls (glass and waxed glass) and three different samples of the nanocoatings with pictures of water drops. Data are present as mean±SD, n=6.

FIG. 7 shows AFM pictures of in vitro nanocoatings, created with different parameters. (a-d) Different ratios of retinin to wax, and different humidity. (e) Mix of BSA with lanolin. (f-h) Nanocoatings with different repeated protocols. (i-l) Mix of retinin solution and lanolin (i), beeswax (j), paraffin (k), or carnauba wax (l) emulsion. Size of AFM images is 2×2 µm.

Figure 8:
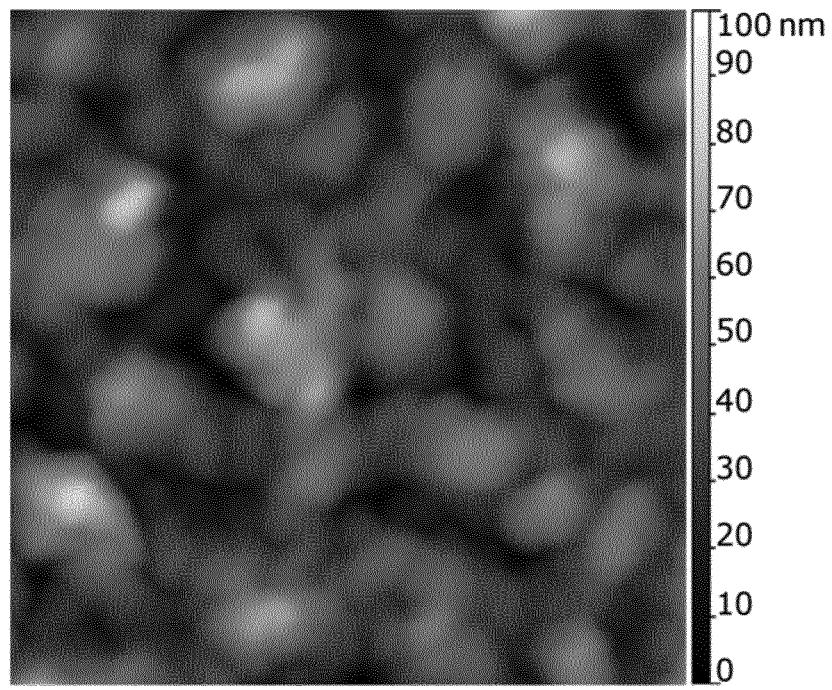

FIG. 8 shows an AFM picture of an in vitro nanocoating created from a mixture of retinin solution and olive oil emulsion. Size of AFM image is 2×2 µm.

FIG. 9 shows a schematic overview of the in vitro nanocoating described herein and other existing nanocoatings. The figure designates whether the nanocoatings possess a selection of characteristic; (i) "3D shape", i.e. can the nanocoating readily be used for three-dimensional surfaces, (ii) "big scale surface", i.e. can the nanocoating be used on large surfaces, (iii) "low process complexity", i.e. does preparation of the nanocoating require advanced and specialized equipment, (iv) "absence of corrosive/toxic chemicals", i.e. can the nanocoating be prepared without damaging the environment, (v) "easy to modify", i.e. can the nanocoating be easily adapted to various applications, (vi) "bio-degradable", i.e. can the components of the nanocoating be degraded in nature. The list of methods as recited in FIG. 9 is based on Nanoscale, 2015,7, 5922-5946.

FIG. 10 shows formation of nanocoatings with the cuticular proteins CPR10 and CG13059. SDS-PAGE of samples from retina and cornea of (a) *D. melanogaster* and (b) *A. gambiae*. Major protein bands unique for cornea were identified by peptide mass-spectrometry. Positions of molecular weight standards are indicated to the right of the gel. Retinin and CPR10 marked by labels. (c) Transmission spectra measured for nanostructures, obtained from CPR10 protein. Theoretical maximum of transmittance is approximately 104%. Representative AFM images (3×3 µm) of samples by using (d) CG13059 protein and (e) CPR10 protein with lanolin wax shows formation of nanostructures.

The present invention will now be described in more detail in the following.

DETAILED DESCRIPTION OF THE INVENTION

Definitions

Prior to discussing the present invention in further details, the following terms and conventions will first be defined:

Coating

In the present context, the term "coating" refers to a covering that extends across the surface of an object. The coating may cover all of the object or only parts of the object.

The coating may provide an object with one or more advantageous functional properties such as, but not limited to, anti-reflectivity, anti-wettability, anti-microbial, self-cleaning, anti-icing, and regulation of attachment and/or growth and/or differentiation of cells and/or tissues.

The terms "coating" and "nanocoating" are used interchangeably herein.

Surface

In the present context, the term "surface" refers to any outer layer of an object on which a coating can be applied to. The surface may have any form (e.g. flat, spherical, elongated, cylindrical etc.), and be of a material such as, but not limited to, glass, metal, plastic, polymer, silicon, minerals, paper and concrete. The surface may be comprised of a combination of materials.

The surface may be part of any type of product that may benefit from the nanocoatings as described herein. Thus, the surface may be an outer layer of a product such as, but not limited to, contact lenses, glass-containing surfaces, displays, solar panels, artistic paintings, biological implants, construction materials, and electric wires.

Solution

In the present context, the term "solution" refers to a medium consisting of a solvent and a range of ingredients, which are all entirely dissolved, in said solvent. Thus, a solution does not comprise any solid dispersed material, i.e. it is not a suspension. Also, a solution does not comprise other liquid immiscible components, i.e. the solution is not an emulsion.

Retinin or Retinin-Like Protein

In the present context, the term "retinin or retinin-like protein" refers to a protein expressed in the eye or cornea of a variety of insects and which preferably comprises a conserved region known as the retinin C-domain. However, "retinin-like proteins" also includes proteins which does not comprise the retinin C-domain, but wherein the remaining part of the amino acid sequence is similar to the middle and C-terminus parts of the Retinin sequence (disregarding the signal peptide sequence). The retinin C-domain is designated PF04527 in the PFAM database of protein families and is also known as Retinin-like domain designated IPR007614 in the InterPro database of proteins.

The term "retinin or retinin-like protein" as used herein allow also for a certain degree of homology in their common retinin C-domain region or other regions of the protein. Therefore, the amino acid sequence of the protein may deviate from the sequence identified above and thus vary between retinin or retinin-like proteins described herein.

Cuticular Proteins

In the present context cuticular proteins are proteins found in the exoskeleton of arthropod organisms, hereunder insects. The cuticula or cuticle is a multi-layered structure outside the epidermis of many invertebrates, notably arthropods, in which it forms an exoskeleton. Thus cuticle proteins form the major part of the integument of arthropods. The integument is the natural covering of an organism or an organ, such as its skin, husk, shell, or rind. Thus, it includes most of the material of the exoskeleton of the insects.

Emulsion

In the present context, the term "emulsion" refers to a mixture of at least two liquids, which under normal conditions are immiscible. The emulsion is a two-phase system wherein one liquid, i.e. the dispersed phase, is dispersed in the other, i.e. the continuous phase. The dispersed phase may be present as droplets.

The typical emulsion is a classical two-phase system, such as oil-in-water wherein the oil is the dispersed phase and water is the continuous phase or water-in-oil wherein the water is the dispersed phase and oil is the continuous phase. However, multiple emulsions such as water-in-oil-in-water emulsion and an oil-in-water-in-oil emulsion are also possible.

The constituents of the emulsion is not limited to water and oil as exemplified above, but may be other liquids. Thus, in the present context, lipids may be a constituent of an emulsion.

Emulsifiers may be used to stabilize the emulsion. Typical emulsifiers are compounds with polar and non-polar part and include, but are not limited to, surfactants and detergents.

Suspension

In the present context, the term "suspension" refers to a mixture that comprises solid particles (i.e. the solute) suspended in a solvent.

The suspension may be either a classical suspension in which the solute is of size sufficiently large to sediment or be a colloidal suspension in which the solute (or colloid) are particles of a size that do not readily sediment. Thus, in the classical suspension, particles are typically of sizes larger than 1 µm and in the colloidal suspension, the particles are typically in the nanometer scale, i.e. 1-1000 nm.

Lipid

In the present context, the term "lipid" refers to hydrophobic or amphiphilic molecules that are soluble in non-polar solvents and do not easily dissolve in water. Lipids include, but are not limited to, waxes, fats, oils, sterols, phospholipids, and mono-, di- and tri-glycerides.

Generally, oils are lipids that are liquid at room temperature, whereas fats are lipids that are solid at room temperature.

Wax

In the present context, the term "wax" refers to compounds that are lipophilic, malleable solids near room temperature. Thus, at room temperature, waxes display an elevated ability to deform under compressive stress. Typically, waxes have melting points above 40° C.

Waxes appear as unctuous, meltable, viscous liquids to solid substances, having a characteristic waxy luster, and may be of natural or synthetic origin or derived from natural or synthetic materials.

Waxes include hydrophobic or amphiphilic higher alkanes that are soluble in non-polar solvents, but insoluble in water. Waxes may encompass various functional groups such as, but not limited to, fatty acids, alcohols, unsaturated bonds, aromatics, amides, ketones and aldehydes.

Specifically, many waxes comprise fatty acid esters. These waxes are made from a fatty acid bonded through an ester linkage to an alcohol.

In contrast, paraffin wax is an example of a wax comprised of a mixture of long-chain hydrocarbons without functional groups.

Insect

In the present context, the term "insect" refers to animals of the subclass *Pterygota*, which is a subclass to the class Insecta. The subclass *Pterygota* comprises all the winged insects.

More specifically, the retinin or retinin-like protein or cuticular protein may be obtained from any animal within the subclass *Pterygota* suitable for providing the retinin, retinin-like protein or cuticular protein. Similarly, the retinin or retinin-like protein or cuticular protein may be provided as a recombinant protein based on the amino acid (or initially nucleic acid) of any animal within the subclass *Pterygota*, which express retinin, retinin-like or cuticular protein protein.

Recombinant

In the present context, the term "recombinant" when referring to a protein, means that a protein is derived from recombinant (e.g. microbial, insect or mammalian) expression systems.

Sequence Identity

In the present context, the term "identity" is here defined as the sequence identity between genes or proteins at the nucleotide, base or amino acid level, respectively. Specifically, a DNA and a RNA sequence are considered identical if the transcript of the DNA sequence can be transcribed to the identical RNA sequence.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

In another embodiment, the two sequences are of different length and gaps are seen as different positions. One may manually align the sequences and count the number of identical amino acids. Alternatively, alignment of two sequences for the determination of percent identity may be accomplished using a mathematical algorithm. Such an algorithm is incorporated into the NBLAST and XBLAST programs of Altschul et al. 1990. BLAST nucleotide searches may be performed with the NBLAST program, score=100, word length=12, to obtain nucleotide sequences homologous to a nucleic acid molecules of the invention. BLAST protein searches may be performed with the XBLAST program, score=50, word length=3 to obtain amino acid sequences homologous to a protein molecule of the invention.

To obtain gapped alignments for comparison purposes, Gapped BLAST may be utilized. Alternatively, PSI-Blast may be used to perform an iterated search, which detects distant relationships between molecules. When utilising the NBLAST, XBLAST, and Gapped BLAST programs, the default parameters of the respective programs may be used. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted. An embodiment of the present invention thus relates to sequences of the present invention that has some degree of sequence variation.

Method for Formation of In Vitro Nanocoatings

The ideal material for production of a product may not always have the desired surface properties. Examples of this scenario include slippery flooring, degradation prone materials, overly reflective glass etc. Functional coatings may be applied to change the surface properties of such materials and mend any shortcomings of properties. Nanostructured coatings have been used to design materials and products with new properties such as anti-friction, thermal resistance, chemical inertness, self-cleaning or protective effects, but common for fabrication of these nanocoatings is that they are produced using harsh processes that are not compatible with soft matter materials sensitive to harsh treatment.

The present invention aims at providing means for in vitro coating of any type of surface, including soft matter materials sensitive to harsh treatment. Thus, the present invention relates to a simple and cheap method for producing functional nanocoatings on natural or artificial surfaces using biologic reagents under mild conditions.

The inventors of the present invention, noted that terrestrial arthropods carry elaborated nanocoatings on top of their corneal surfaces. Serving an antireflective function (and potentially anti-wetting, bactericidal, and dirt-removing purposes), these nanocoatings in different arthropods can be built by nanoscale paraboloid protrusions (nipples), ridges, mazes, dimples, or various transitions among these forms. Based on this observation, the inventors set out to identify the key components for formation of these natural nanocoatings, with the aim of recreating the nanocoatings in an in vitro setting.

The inventors hypothesized that the terrestrial arthropods nanocoatings were composed of two chemical entities, possessing different diffusion and/or hydrophobicity properties and antagonistically interacting with each other. Utilizing *Drosophila* as the model insect, the corneal protein retinin in combination with lipids are identified as the minimal components for formation of natural nanocoatings. Cuticular proteins from insects have also been found to behave similarly to retinin in this respect.

Surprisingly, the inventors found that it is possible to recreate the nanocoatings on artificial surfaces through the admixing of e.g. retinin and commercial lipids. By varying the admixing procedure, the method may be used to produce a diverse set of nanocoatings yielding different functionalities. Importantly, the bioinspired nanocoating is produced under mild conditions and uses natural reagents that are easily accessible.

Thus, an aspect of the present invention relates to a method for preparation of a coated surface, said method comprising the following steps:
 i. providing a protein solution comprising retinin or retinin-like protein,
 ii. providing an emulsion or suspension comprising one or more lipids,
 iii. mixing said protein solution and said emulsion or suspension to provide a liquid mixture,
 iv. contacting a surface with said liquid mixture, and
 v. drying said surface,
thereby providing a coated surface.

An alternative aspect of the invention relates to a method for preparation of a coated surface, said method comprising the following steps:
 i. providing a protein solution comprising retinin, retinin-like protein, or cuticular protein,
 ii. providing an emulsion or suspension comprising one or more lipids,
 iii. mixing said protein solution and said emulsion or suspension to provide a liquid mixture,
 iv. contacting a surface with said liquid mixture, and
 v. drying said surface,
thereby providing a coated surface.

In a preferred embodiment of this aspect the retinin, retinin-like protein, or cuticular protein may alternatively be expressed as selected from the group consisting of retinin, retinin-like protein, and cuticular protein. Preferably, retinin, retinin-like protein, or cuticular protein is retinin or retinin-like protein. Mixtures of the three protein types may also be comprised in the protein solution.

Cuticular proteins may be found throughout the fauna of nature and include, but are not limited to, cuticular proteins from arthropod organisms, hereunder insects. These proteins are found in the surface of the exoskeleton of arthropods including insects, and may thus preferably be insect cuticular protein.

Another embodiment relates to the method as described herein, wherein the retinin, retinin-like protein, or cuticular protein originates from an arthropod or insect, and is able to bind physically to lipids, such as waxes. A further embodiment of the present invention relates to the method as described herein, wherein the retinin, retinin-like protein, or cuticular protein comprises a secretory signal peptide and/or have a size in the range of 10 kDa to 35 kDa.

Retinin is a protein that are restricted in its expression to the cornea of insects. It belongs to the group of small insect proteins possessing the functionally uncharacterized retinin C-domain. Although insects constitute a diverse group of animals, the retinin protein is predicted to be present in several distinct orders of insect whose genomes have been sequenced to-date (see e.g. PFAM database of EMBL-EBI).

Thus, an embodiment of the present invention relates to the method as described herein, wherein the retinin, retinin-like protein, or cuticular protein originates from an insect belonging to the order *Diptera*.

Another embodiment of the present invention relates to the method as described herein, wherein the insect belongs to a family selected from the group consisting of Drosophilidae, Culicidae, Calliphoridae, Phoridae, Tephritidae, Psychodidae, Muscidae, Chironomidae, Corethrellidae, and Glossinidae.

A further embodiment of the present invention relates to the method as described herein, wherein the insect belongs to a genus selected from the group consisting of *Drosophila*, *Anopheles*, *Culex*, *Aedes*, *Wyeomiya*, *Lucilia*, *Megaselia*, *Bactrocera*, *Lutzomiya*, *Phlebotomus*, *Musca*, *Stomoxys*, *Clunio*, *Corethrella*, *Ceratitis*, and *Glossina*.

Yet another embodiment of the present invention relates to the method as described herein, wherein the insect is a species selected from the group consisting of *D. melanogaster*, *D. virilis*, *D. busckii*, *D. erecta*, *D. simulans*, *D. yakuba*, *D. sechellia*, *D. pseudoobscura*, *D. ananassae*, *D. persimilis*, *D. suzukii*, *D. grimshawi*, *D. willistoni*, *D. mojavensis*, *D. ficusphila*, *Anopheles gambiae*, *Anopheles darlingi*, *Anopheles sinensis*, *Anopheles aquasalis*, *Anopheles albimanus*, *Anopheles arabiensis*, *Anopheles atroparvus*, *Anopheles christyi*, *Anopheles coluzzii*, *Anopheles culicifacies*, *Anopheles dirus*, *Anopheles epiroticus*, *Anopheles farauti*, *Anopheles funestus*, *Anopheles maculatus*, *Anopheles melas*, *Anopheles merus*, *Anopheles minimus*, *Anopheles quadriannulatus*, *Anopheles stephensi*, *Culex quinquefasciatus*, *Aedes aegipty*, *Aedes albopictus*, *Wyeomiya smithii*, *Lucilia cuprina*, *Megaselia scalaris*, *Bactrocera cucurbitae*, *Bactroteca latifrons*, *Bactrocera dorsalis*, *Lutzomiya longipalsis*, *Phlebotomus papatasi*, *Musca domestica*, *Stomoxys calcitrans*, *Clunio marinus*, *Corethrella appendiculata*, *Ceratitis capitata*, *Glossina brevipalpis*, *Glossina fuscipes*, *Glossina pallidipes*, *Glossina palpalis*, *Glossina morsitans*, and *Glossina austeni*.

In *A. gambiae*, the protein CPR10 (SEQ ID NO:8) found in the eye was identified as a retinin-like protein involved in nanostructure formation. An embodiment of the present invention relates to the method as described herein, wherein the insect is *Anopheles gambiae*.

Another embodiment of the present invention relates to the method as described herein, wherein the retinin or retinin-like protein or cuticular protein comprises an amino acid sequence selected from:
 (i) SEQ ID NO:8, or
 (ii) an amino acid sequence having at least 80% sequence identity to the sequence in (i), such as at least 85%, at least 90%, at least 95%, at least 96%, at least 97%, at least 98%, or at least 99% sequence identity to the sequence in (i).

It is to be understood that retinin or retinin-like proteins or cuticular protein comprising amino acid sequences according to (ii), retains the ability to form nanocoatings as described herein.

An extensively studied genus of insects is *Drosophila*, an in particular *D. melanogaster*, which has served as model for many basic research studies. Herein, proteomic characterization of a large group of species within the *Drosophila* genus revealed a protein composition similar to that of *D. melanogaster*, including the presence of the retinin protein. These findings support the notion that retinin is an important structural protein found in a large variety of insects.

Therefore, an embodiment of the present invention relates to the method as described herein, wherein the insect belongs to the genus *Drosophila*.

Another embodiment of the present invention relates to the method as described herein, wherein the insect is a species selected from the group consisting of *D. melanogaster, D. virilis, D. busckii, D. erecta, D. simulans, D. yakuba, D. sechellia, D. pseudoobscura, D. ananassae, D. persimilis, D. suzukii, D. grimshawi, D. willistoni, D. mojavensis*, and *D. ficusphila*.

A preferred embodiment of the present invention relates to the method as described herein, wherein the insect is *D. melanogaster*.

In the *Drosophila* species, numerous retinin-like genes are present on the same locus of the chromosome arm 3L, suggestive of recent duplication events. The data available from the *Drosophila* gene expression atlas (FlyAtlas) shows that the retinin-like genes from this cluster are expressed in other tissues than the eye, where retinin is strongly expressed. Many of these encode the retinin C-domain, including, but not limited to, CG13044, CG13062, CG13040, CG4962, CG13041, CG13042, CG13043, CG13060, CG4982 and CG13063. Thus, an embodiment of the present invention relates to the method as described herein, wherein the retinin or retinin-like protein is selected from the group consisting of CG13044, CG13062, CG13040, CG4962, CG13041, CG13042, CG13043, CG13060, CG4982 and CG13063.

Furthermore, in *D. melanogaster*, the protein CG13059 (SEQ ID NO:9) was identified as a retinin-like protein involved in nanostructure formation.

An embodiment of the present invention relates to the method as described herein, wherein the retinin or retinin-like protein comprises an amino acid sequence selected from:
  (i) SEQ ID NO:9, or
  (ii) an amino acid sequence having at least 80% sequence identity to the sequence in (i), such as at least 85%, at least 90%, at least 95%, at least 96%, at least 97%, at least 98%, or at least 99% sequence identity to the sequence in (i).

It is to be understood that retinin or retinin-like proteins comprising amino acid sequences according to (ii), retains the ability to form nanocoatings as described herein.

An aspect of the present invention relates to a method for preparation of a coated surface, said method comprising the following steps:
  i. providing a protein solution comprising CPR10 (SEQ ID NO:8) or CG13059 (SEQ ID NO:9),
  ii. providing an emulsion or suspension comprising one or more lipids,
  iii. mixing said protein solution and said emulsion or suspension to provide a liquid mixture,
  iv. contacting a surface with said liquid mixture, and
  v. drying said surface,
thereby providing a coated surface.

Another aspect of the present invention relates to a coated surface comprising CPR10 (SEQ ID NO:8) or CG13059 SEQ ID NO:9) and one or more lipids.

An additional embodiment of the present invention relates to the method as described herein, wherein the retinin, retinin-like protein, or cuticular protein originates from an insect belonging to the subclass *Pterygota*.

As described herein, the inventors have identified the molecular mechanism and the building constituents of the insect corneal nanostructures. Given the biologic constituents of the nanocoatings, an aim of the present invention is to establish a simple and cheap protocol for production of corneal type nanocoatings.

By recombinant expression of retinin, retinin-like protein, or cuticular protein in a suitable expression system followed by purification of the recombinant protein, relatively large yields of recombinant retinin, retinin-like protein, or cuticular protein can be obtained. This protocol is based on well-known techniques, such as *E. coli* recombinant protein expression and standard Ni-NTA purification, and therefore should be readily accessible without need for advanced and expensive equipment.

Thus, an embodiment of the present invention relates to the method as described herein, wherein the retinin, retinin-like protein, or cuticular protein is recombinant retinin, retinin-like protein, or cuticular protein.

The second constituent of the nanocoatings, lipids, is likewise easily accessible as commercially available off-the-shelf products that can be purchased relatively cheap in a plethora of different variants. Thus, the method as described herein is (i) simple as the protocol is based on a series of admixing, washing and drying steps and (ii) cheap because the two main constituents can be obtained in ample quantities without a large investment. Furthermore, the simple preparation of the corneal type nanocoatings facilitates high-throughput production of (anti-reflective) coated surfaces at rates that surpass the normal output rate of conventional technologies such as etching or lithographic techniques.

Without being bound by theory, the inventors hypothesize that the importance of retinin in the formation of corneal nanocoatings is linked to the common retinin C-domain that is shared among retinin and retinin-like proteins of a variety of insects.

Therefore, an embodiment of the present invention relates to the method as described herein, wherein the retinin or retinin-like protein comprises the common Retinin C-domain designated PF04527 as described in the PFAM database of protein families, also known as Retinin-like domain designated IPR007614 as described in the InterPro database of proteins.

Another embodiment of the present invention relates to the method as described herein, wherein the retinin or retinin-like protein comprises an amino acid sequence selected from
  i. SEQ ID NO: 1, or
  ii. an amino acid sequence having at least 80% sequence identity to the sequence in (i).

A further embodiment of the present invention relates to the method as described herein, wherein the retinin or retinin-like protein comprises an amino acid sequence as defined by SEQ ID NO: 1.

An even further embodiment of the present invention relates to the method as described herein, wherein the retinin or retinin-like protein comprises an amino acid sequence selected from
  i. SEQ ID NO: 2, or
  ii. an amino acid sequence having at least 80% sequence identity to the sequence in (i).

A still further embodiment of the present invention relates to the method as described herein, wherein the retinin or retinin-like protein comprises an amino acid sequence as defined by SEQ ID NO: 2

Another embodiment of the present invention relates to the method as described herein, wherein the retinin or retinin-like protein comprises the amino acid sequence selected from
i. SEQ ID NO: 3, or
ii. an amino acid sequence having at least 80% sequence identity to the sequence in (i).

Yet another embodiment of the present invention relates to the method as described herein, wherein the retinin or retinin-like protein comprises an amino acid sequence as defined by SEQ ID NO: 3.

A further embodiment of the present invention relates to the method as described herein, wherein the retinin or retinin-like protein comprises an amino acid sequence having at least 80% sequence identity to SEQ ID NO: 1, SEQ ID NO:2, or SEQ ID NO:3, such as at least 85%, at least 90%, at least 95%, at least 96%, at least 97%, at least 98%, or at least 99% sequence identity to SEQ ID NO: 1, SEQ ID NO:2, or SEQ ID NO:3.

It is to be understood that retinin or retinin-like proteins comprising an amino acid sequence having at least 80% sequence identity to SEQ ID NO: 1, SEQ ID NO:2, or SEQ ID NO:3, retains the ability to form nanocoatings as described herein.

An even further embodiment of the present invention relates to the method as described herein, wherein the retinin or retinin-like protein is selected from an amino acid sequence represented by SEQ ID NO:1, SEQ ID NO:2 or SEQ ID NO:3.

The nanocoatings described herein provides the coated surface with properties directly derivable from the formed nanopatterns on the surface, e.g. anti-reflectivity, anti-wetting etc. However, it is possible to endow the coated surface with additional properties through modification of the recombinant retinin, retinin-like protein, or cuticular protein. Thus, the recombinant production of retinin, retinin-like protein, or cuticular protein may be preceded by a design phase in which modification to the protein is schemed to obtain a desirable functionality. Modification of the protein may be carried out using standard molecular biology techniques known to the person skilled in the art.

Thus, an embodiment of the present invention relates to the method as described herein, wherein the retinin, retinin-like protein, or cuticular protein comprises one or more modifications.

Another embodiment of the present invention relates to the method as described herein, wherein the one or more modifications are selected from the group consisting of a fluorescent label, a radioactive label, a metal capturing moiety, an antibody-binding site, and an enzyme-binding site.

The proteins of the invention can be readily obtained, e.g. by recombinant expression in bacteria, as described herein. For efficient formation of nanocoatings, only relatively low concentrations of protein is required. The low consumption of material ensure that costs of the method are kept at a minimal.

Therefore, an embodiment of the present invention relates to the method as described herein, wherein the concentration of retinin, retinin-like protein, or cuticular protein in the protein solution is from 0.1 mg/mL to 2.0 mg/mL, such as from 0.2 mg/mL to 1.5 mg/mL, such as 0.3 mg/mL to 1.0 mg/mL, such as 0.4 mg/mL to 0.8 mg/mL, such as 0.5 mg/mL to 0.7 mg/mL, preferably 0.6 mg/mL.

The solvent of the protein solution or the emulsion or suspension comprising lipids may be adjusted to induce proper nanocoating formation. The solvent may comprise e.g. salts to regulate stability and interaction of the main constituents of the nanocoating.

Thus, an embodiment of the present invention relates to the method as described herein, wherein the protein solution and/or the emulsion or suspension are provided in aqueous solutions.

Another embodiment of the present invention relates to the method as described herein, wherein the aqueous solutions are solutions comprising at least one salt, such as saline solutions.

A further embodiment of the present invention relates to the method as described herein, wherein the aqueous solutions comprise a buffering system selected from the group consisting of TRIS, phosphate, HEPES, MOPS, and PIPES.

Beside protein, the second main constituent for nanocoating formation is lipid. Lipids are hydrophobic or amphiphilic molecules, that include e.g. waxes, fats, oils, sterols, phospholipids, and mono-, di- and tri-glycerides.

Therefore, an embodiment of the present invention relates to the method as described herein, wherein the one or more lipids are selected from the group consisting of waxes, fats, oils, sterols, phospholipids, and mono-, di- and tri-glycerides.

A characteristic of many lipids is the presence of one or more long carbon chains, which renders at least part of the lipid hydrophobic in nature. The hydrophobicity of the lipids governs their distribution in solution and interaction with retinin, retinin-like protein, or cuticular protein. Without being bound by theory, the inventors hypothesize that the size of carbon chains of the lipids influence the morphology of the nanocoating and therefore potentially the resulting functionality.

Therefore, an embodiment of the present invention relates to the method as described herein, wherein the one or more lipids are molecules comprising one or more carbon chains comprising at least 10 carbons atoms, such as at least 12 carbon atoms, such as at least 15 carbon atoms, such as at least 20 carbon atoms, such as at least 25 carbon atoms, such as at least 30 carbon atoms.

Waxes malleable substances that include hydrophobic or amphiphilic higher alkanes that are soluble in non-polar solvents, but insoluble in water. Typically, waxes are comprised of a mixture of long-chain hydrocarbons with or without functional groups. This group of lipids form highly structured nanocoatings when combined with proteins of the invention.

Thus, an embodiment of the present invention relates to the method as described, wherein the one or more lipids are waxes.

Waxes may be obtained from many sources, with most waxes being readily accessible as commercial products.

Consequently, an embodiment of the present invention relates to the method as described herein, wherein the wax is selected from the group consisting of a plant wax, animal wax, petroleum derived wax, mineral wax and synthetic wax.

Plant waxes include, but are not limited to, carnauba, quericury, palm, raffia, cocoa, candelilla, rhimba, ocoxilla, banana, esparto, flax, hemp, cottonseed, kapok, sugar cane, banaboo leaf, bayberry, ucuhuba, japan, cocoa butter, fiber, reed, godang and blanophore waxes. Animal waxes include, but are not limited to, lanolin, spermaceti, beeswax, stearic acid, Chinese insect wax and shellac wax. Petroleum derived waxes include, but are not limited to, microcrystalline wax, Montan wax, and peat wax. Mineral waxes include, but are not limited to, ozokerite, paraffin, ceresin and petrolatum. Synthetic waxes include, but are not limited to, fatty acids, fatty alcohols, esters of higher-atom alcohols and fatty acids, glycerol esters, mono and di-fatty acids esters of glycols, hydrogenated and partially hydrogenated fatty oils, and polyglycols.

Another embodiment of the present invention relates to the method as described herein, wherein the wax is selected from the group consisting of a carnauba wax, beeswax, paraffin wax, lanolin wax, Chinese wax, shellac wax, spermaceti, bayberry wax, candelilla wax, castor wax, esparto wax, Japan wax, ouricury wax, soy wax, tallow tree wax, ceresin waxes, montan wax, ozocerite, peat waxes, microcrystalline wax, individual components and derivatives thereof, and combinations thereof.

A preferred embodiment of the present invention relates to the method as described herein, wherein the wax is selected from the group consisting of lanolin wax, paraffin wax, beeswax and carnauba wax.

A further embodiment of the present invention relates to the method as described herein, wherein the one or more lipids are oils selected from the group consisting of olive oil, grapeseed oil, palm oil, coconut oil, corn oil, rapeseed oil, sesame oil, soybean oil and sunflower oil.

A preferred embodiment of the present invention relates to the method as described herein, wherein the oil is olive oil.

Fats are esters of three fatty acid chains and the alcohol glycerol. Thus, an embodiment of the present invention relates to the method as described herein, wherein the one or more lipids are fats comprising fatty acids selected from the group consisting capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

The formation and final morphology of the nanocoating may be affected by a range of protocol parameters that can be adjusted to induce formation of a homogeneous nanocoating.

Thus, an embodiment of the present invention relates to the method as described herein, wherein the pH of the emulsion or suspension is in the range of 5-11, such as 7-10.5, such as 8-10, such as 8.5-9.5, preferably approximately 9.

Another embodiment of the present invention relates to the method as described herein, wherein drops of lipids in the emulsion or suspension is of a diameter of less than 500 nm.

A further embodiment of the present invention relates to the method as described herein, wherein ratio (vol/vol) of protein solution to emulsion or suspension is in a range of 1:1 to 1:10, such as 1:2 to 1:5, preferably 1:3.

An even further embodiment of the present invention relates to the method as described herein, wherein 5 µL of protein solution is mixed with of 15 µL emulsion or suspension.

A still further embodiment of the present invention relates to the method as described herein, wherein the contacting is performed at a temperature in the range of 0-50° C., such as 10-40° C., such as 15-35° C., such as 20-30° C., preferably 25° C.

Another embodiment of the present invention relates to the method as described herein, wherein the contacting is performed at a humidity in the range of 10-90%, such as 35-75%, such as 40-70%, such as 45-65%, preferably at 50%.

Yet another embodiment of the present invention relates to the method as described herein, wherein the surface is dried for at least 5 minutes, such as for at least 10 minutes, such as for at least 15 minutes, preferably for approximately 20 minutes.

The protocol described herein is suitable for use with any type of surface to which the liquid mixture comprising the retinin, retinin-like protein, or cuticular protein and the lipids can adhere. Thus, products made from a wide range of materials may benefit from the nanocoatings described herein. Contact lenses, sunglasses, displays and solar panels are all examples of products in which optical coatings are extensively used to adjust e.g. anti-reflectivity, absorbance etc. Another group of products suited for nanocoating is biological implants on which nanocoatings may regulate in vivo cell and/or tissue attachment, growth and differentiation. Regulation of cell and/or tissue attachment, growth and differentiation may also be achieved in vitro by nanocoating of surfaces and proper laboratory protocols. Especially regulation of attachment, growth and differentiation of cells and/or tissues, such as bone and cartilage cells and/or tissues, as well as stem cells of various types are applications that would benefit from the methods described herein. A broad palette of materials is used for the products as exemplified above.

Therefore, an embodiment of the present invention relates to the method as described herein, wherein the surface is of a one or more materials selected from the group consisting of glass, metal, plastic, polymer, silicon, minerals, paper and concrete.

A preferred embodiment of the present invention relates to the method as described herein, wherein the surface is of glass.

For some applications, depending on the constituents of the nanocoating and the targeted surface, it may be favorable to extend the protocol to encompass additional process steps, such as washing, drying and material deposition on the surface.

Thus, an embodiment of the present invention relates to the method as described herein, wherein the method further comprises the additional step of vi. washing the surface, and vii. redrying the surface Benefits of additional washing/drying include more homogeneous nanocoatings and the removal of residual unbound constituents of the liquid mixture comprising protein and lipids. The solvent used for washing of the surface is preferably an aqueous solvent, such as water or alcohols.

Therefore, an embodiment of the present invention relates to the method as described herein, wherein the solvent for washing is selected from the group consisting of aqueous solutions, ethanol, and polar solvents.

Another embodiment of the present invention relates to the method as described herein, wherein the solvent used for washing is water.

A further embodiment of the present invention relates to the method as described herein, wherein the method is repeated two or more times on the coated surface.

A still further embodiment of the present invention relates to the method as described herein, wherein the method is repeated using a liquid mixture which does not comprise the emulsion or suspension.

The inventors have surprisingly found that corneal nanocoatings can be re-synthesized in vitro by the mere admixing of two simple constituents. Retinin and lipids are the two key constituents jointly regulating formation and diversity of the corneal type nanostructures. The in vitro nanocoatings are reminiscent of the natural insect nanocoatings and display both stability and functionalities, such as anti-reflection and anti-wetting.

Thus, an aspect of the present invention relates to a coated surface obtainable by mixing
- a protein solution comprising retinin, retinin-like protein, or cuticular protein, with
- an emulsion or suspension comprising one or more lipids to provide a liquid mixture,
- and contacting said surface with said liquid mixture followed by drying said surface.

Thus, an embodiment of the present invention relates to a coated surface obtainable by a method as described herein. Another embodiment of the present invention relates to a coated surface obtained by a method as described herein.

Another aspect of the present invention relates to a coated surface comprising retinin, retinin-like protein, or cuticular protein and one or more lipids.

The retinin and cuticular proteins are predicted to be present in several distinct orders of insect whose genomes have been sequenced to-date, such as *Diptera*. Furthermore, retinin is ubiquitously found in different genera within the Drosophilidae family (see e.g. PFAM database of EMBL-EBI).

Therefore, an embodiment of the present invention relates to the coated surface as described herein, wherein the retinin, retinin-like protein, or cuticular protein originates from an insect belonging to a genus selected from the group consisting of *Drosophila, Anopheles, Culex, Aedes, Wyeomiya, Lucilia, Megaselia, Bactrocera, Lutzomiya, Phlebotomus, Musca, Stomoxys, Clunio, Corethrella, Ceratitis,* and *Glossina*.

Another embodiment of the present invention relates to the coated surface as described herein, wherein the insect belongs to the genus *Drosophila*.

A preferred embodiment of the present invention relates to the coated surface as described herein, wherein the insect is a species selected from the group consisting of *D. melanogaster, D. virilis, D. busckii, D. erecta, D. simulans, D. yakuba, D. sechellia, D. pseudoobscura, D. ananassae, D. persimilis, D. suzukii, D. grimshawi, D. willistoni, D. mojavensis,* and *D. ficusphila*.

As described previously, easy access to sufficient quantities of protein is ensured by recombinant expression of the protein. No specific expression system is required to obtain sufficient amounts of retinin, retinin-like protein, or cuticular protein. Herein, expression of retinin is exemplified in *E. coli* using a plasmid expression vector, but the person skilled in the art would be able to substitute with other suitable expression systems as well. Recombinant expression is versatile in that the proteins may be a certain degree of homology in their common retinin C-domain region or other regions of the protein.

Therefore, an embodiment of the present invention relates to the coated surface as described herein, wherein the retinin, retinin-like protein, or cuticular protein is recombinant retinin or recombinant retinin-like protein or recombinant cuticular protein.

Another embodiment of the present invention relates to the coated surface as described herein, wherein the retinin or retinin-like protein comprises an amino acid sequence selected from
i. SEQ ID NO: 1, or
ii. an amino acid sequence having at least 80% sequence identity to the sequence in (i).

A further embodiment of the present invention relates to the coated surface as described herein, wherein the retinin or retinin-like protein comprises an amino acid sequence selected from
i. SEQ ID NO: 2, or
ii. an amino acid sequence having at least 80% sequence identity to the sequence in (i).

Yet another embodiment of the present invention relates to the coated surface as described herein, wherein the retinin or retinin-like protein comprises the amino acid sequence selected from
i. SEQ ID NO: 3, or
ii. an amino acid sequence having at least 80% sequence identity to the sequence in (i).

A further embodiment of the present invention relates to the coated surface as described herein, wherein the retinin or retinin-like protein comprises an amino acid sequence having at least 80% sequence identity to SEQ ID NO: 1, SEQ ID NO:2, or SEQ ID NO:3, such as at least 85%, at least 90%, at least 95%, at least 96%, at least 97%, at least 98%, or at least 99% sequence identity to SEQ ID NO: 1, SEQ ID NO:2, or SEQ ID NO:3.

It is to be understood that retinin or retinin-like proteins comprising an amino acid sequence having at least 80% sequence identity to SEQ ID NO: 1, SEQ ID NO:2, or SEQ ID NO:3, retains the ability to form nanocoatings as described herein.

As described herein, the inventors have identified lipids as the second constituent of the corneal type nanocoatings antagonistically interacting with retinin, retinin-like protein, or cuticular protein. Lipids are hydrophobic or amphiphilic molecules, that include e.g. waxes, fats, oils, sterols, phospholipids, and mono-, di- and tri-glycerides. A common characteristic for lipids is presence of long hydrocarbons chains, of which the subgroup of waxes in most cases comprise a mixture of.

Therefore, an embodiment of the present invention relates to the coated surface as described, wherein the one or more lipids are molecules comprising one or more carbon chains comprising at least 10 carbons atoms, such as at least 12 carbon atoms, such as at least 15 carbon atoms, such as at least 20 carbon atoms, such as at least 25 carbon atoms, such as at least 30 carbon atoms.

Another embodiment of the present invention relates to the coated surface as described, wherein the one or more lipids are waxes.

Yet another embodiment of the present invention relates to the coated surface as described, wherein the wax is selected from the group consisting of a plant wax, animal wax, petroleum derived wax, mineral wax and synthetic wax.

A still further embodiment of the present invention relates to the coated surface as described, wherein the wax is selected from the group consisting of a carnauba wax, beeswax, paraffin wax, lanolin wax, Chinese wax, shellac wax, spermaceti, bayberry wax, candelilla wax, castor wax, esparto wax, Japan wax, ouricury wax, soy wax, tallow tree wax, ceresin waxes, montan wax, ozocerite, peat waxes, microcrystalline wax, individual components and derivatives thereof, and combinations thereof.

The material of the surface to be coated depends largely of the nature of the product. Some products require the material to be rigid, curvy, elastic or transparent, thereby indirectly predisposing the use of some materials. The coated surfaces as described herein is not limited to a specific group of materials and the nanostructured patterns making up the nanocoating may be formed on any material and on all geometries as opposed to some conventional techniques for formation of coatings that may be restricted to e.g. flat geometry or hard materials.

Thus, an embodiment of the present invention relates to the coated surface as described herein, wherein the surface is of a one or more materials selected from the group consisting of glass, metal, plastic, polymer, silicon, minerals, paper and concrete.

Another embodiment of the present invention relates to the coated surface as described herein, wherein the retinin, retinin-like protein, or cuticular protein and one or more lipids are arranged in a nanostructured pattern.

It is not feasibly to harvest the naturally occurring surfaces for the purpose of high throughput industrial application. Herein is described non-natural coated surfaces which may readily prepared by a process of low complexity, thereby making possible the prospect of big scale surface modification with high versatility. The nanocoatings described herein offers the same advantageous functionalities as the corresponding nanocoatings naturally occurring on the corneal surfaces of the eyes of a selection of insects, e.g. anti-reflectivity etc. Thus, an embodiment of the present invention relates to the coated surface as described herein, wherein the surface is not a surface of an insect eye.

Another embodiment of the present invention relates to the coated surface as described herein, wherein the surface is not a surface of an insect.

Another embodiment of the present invention relates to the coated surface as described herein, wherein the surface is not a surface of an arthropod.

A further embodiment of the present invention relates to the coated surface as described herein, wherein the surface is not a naturally occurring surface.

The nanostructured pattern of the nanocoatings is comprised of an array of nipple-like protrusions. Individual nipple-like nanostructures can upon a threshold fuse into elongated ridges depending on the degree of order in the packing of the nipple-like protrusions. Consequently, the morphology of the nanopatterns correlates with the level of retinin expression for each species, as the nipple-to-ridge species possess significantly more retinin in their corneae than the nipple-only species (FIG. 3b). This morphological transition may be used to alter the resulting functionalities of the nanocoating.

Therefore, an embodiment of the present invention relates to the coated surface as described herein, wherein the nanostructured pattern is comprised of protrusions and/or ridges.

Another embodiment of the present invention relates to the coated surface as described herein, wherein the protrusions are connected by the ridges.

A further embodiment of the present invention relates to the coated surface as described herein, wherein the width of the protrusions is from 200-400 nm and the height of the protrusions is from 20-100 nm.

Other types of insect corneal nanocoatings have been described, encompassing e.g. maze-like, dimple-type patterns. Functional roles, e.g. anti-reflectivity, has been ascribed to these nanocoatings. It is conceivable that upon modulation of (i) the retinin or retinin-like protein levels, (ii) the exact sequence of retinin or the retinin-like protein, (iii) the ratio and identity of the admixed lipids, and/or (iv) the exact admixing conditions, such other natural nanocoatings with useful applications can also be reproduced in vitro using the methods as described herein.

The nanocoating can be further functionalized by inclusion of one or more modifications. The modifications of the coated surface may be either positioned and/or attached directly of the surface or as part of the nanocoating. Thus, the modification may be part of one of the constituents of the nanocoating, e.g. a part of the recombinant retinin, retinin-like protein, or cuticular protein.

Therefore, an embodiment of the present invention relates to the coated surface as described herein, wherein the coated surface further comprises one or more modifications selected from the group consisting of a fluorescent label, a radioactive label, a surface-bound metal, an antibody, and an enzyme.

The coated surface may find wide applicability in industries consuming functionalized surfaces for use in e.g. contact lenses, glass-containing surfaces, displays, solar panels, artistic paintings, biological implants, and electric wires. The requirement for surface functionalization is founded on very different needs as evidenced by the large variability of the above types of products. Thus, it is important that (i) the technology can be modulated to provide a diversified set of functionalities and (ii) the technology is applicable to a wide range of products.

Therefore, an embodiment of the present invention relates to the coated surface as described herein, wherein the surface has one or more properties selected from the group consisting of anti-reflectivity, anti-wettability, anti-microbial, self-cleaning, anti-icing, and regulation of attachment and/or growth and/or differentiation of cells and/or tissues.

A preferred embodiment of the present invention relates to the coated surface as described herein, wherein the surface has anti-reflectivity and anti-wettability properties.

The surface nanocoatings as described herein may be used for regulation of attachment and/or growth and/or differentiation of cells and/or tissues, such as bone and cartilage cells and/or tissues, as well as stem cells of various types. Thus, the coated surface may be positioned on biological implants to facilitate tissue regeneration or the like, or alternative be part of an in vitro tissue engineering setup for reconstruction of artificial tissues or organs.

The nanocoatings is based on the simple liquid mixture comprising two main constituents; (i) retinin, retinin-like protein, or cuticular protein and (ii) lipids. The liquid mixture may readily be applied to a surface to supply the coated surface with new functionalities.

Thus, an embodiment of the present invention relates to use of a mixture of retinin, retinin-like protein, or cuticular protein and lipid for coating the surface of an object. The object (or product) can as described herein be any type of object onto which the nanocoating will adhere. Preferably, the object is contact lenses or a biological implant.

An aspect of the present invention relates to use of a coated surface as described herein to provide a coated product selected from the group consisting of contact lenses, glass-containing surfaces, displays, solar panels, artistic paintings, biological implants, and electric wires.

A preferred embodiment of the present invention relates to the use as described herein, wherein the coated product is contact lenses.

Another embodiment of the present invention relates to the use as described herein, wherein the coated product has one or more properties selected from the group consisting of anti-reflectivity, anti-wettability, anti-microbial, self-cleaning, anti-icing, and regulation of attachment and/or growth and/or differentiation of cells and/or tissues.

A preferred embodiment of the present invention relates to the use as described herein, wherein the coated product is anti-reflective.

It should be noted that embodiments and features described in the context of one of the aspects of the present invention also apply to the other aspects of the invention.

The invention will now be described in further details in the following non-limiting examples.

EXAMPLES

Example 1: Methods for Preparation and Analysis of Samples

*Drosophila* Cultivation and Genetic Manipulations

The following Drosophila lines were used in this study: Oregon R-C(as a wild-type control), GMR-Gal4, spa-Gal4, φX-22A (for germ-line transformation), CG1942$^{f03896}$ (stock #18707, acyltransferase mutant)—obtained from the Bloomington *Drosophila* stock center; UAS-RNAi-Crys (37736 GD), UAS-RNAi-retinin (102711 KK), UAS-RNAi-Cpr72Ec (29452 GD), UAS-RNAi-CG2781 (48139 GD), UAS-RNAi-CG31523 (45226 GD), UAS-RNAi-Baldspot (47521 GD), UAS-RNAi-CG33110 (29689 GD), UAS-RNAi-CG5326 (47681 GD) and UAS-RNAi-CG31522 (37329 GD) lines—from the Vienna Drosophila Resource Center; UAS-CG5326 (stock #1245)—from the FlyORF (Zurich ORFeome Project). *Drosophila melanogaster* fruit flies were raised at 25° C. in pursuance of the conventional fly husbandry guidelines.

cDNA of retinin (DGRC RH08687) was digested by EagI and Bsp120I sites and subcloned into the NotI site of the pUASTattB plasmid followed by sequencing of constructed transgenes using vector-specific primers: GTAACCAGCAACCAAGTA (forward primer 1, SEQ ID NO:4) and GTCCAATTATGTCACACC (reverse primer 1, SEQ ID NO:5). The constructs were used for generation of the transgenic UAS-retinin line through site-specific germ-line transformation of φX-22A line with attP-landing site on the chromosome arm 2L.

The following non-melanogaster *Drosophila* stocks were obtained from the University of California, San Diego Drosophila Stock Center: *D. pseudoobscura* (stock #14011-0121.00), *D. simulans* (14021-0251.001), *D. virilis* (15010-1051.00), *D. erecta* (14021-0224.00), *D. ananassae* (14024-0371.00), *D. mojavensis* (15081-1352.01), *D. yakuba* (14021-0261.00), *D. grimshawi* (15287-2541.00), *D. persimilis* (14011-0111.01), *D. sechellia* (14021-0248.03), *D. suzukii* (14023-0311.00), *D. willistoni* (14030-0811.00), *D. busckii* (13000-0081.00).

Preparation and Analysis of Corneal and Retinal Samples

Corneal and retinal samples were prepared by cutting off eyes with a scalpel from the heads of mature adult guillotined *Drosophila*. The retinal material was removed from immobilized samples into a drop of water by washing and very gentle and scrupulous scratching. After separation, the corneal material was further washed 3 times in water. Corneal and retinal samples were collected from material of 20 eyes. The samples were boiled 15 min in Sample Buffer (62.5 mM Tris-HCl pH 6.8; 10% glycerol; 2% SDS; 1% β-Mercaptoethanol; trace of bromophenol blue) prior to separation by 15% SDS-PAGE.

Mass-Spectrometry

In-gel trypsin digestion and mass-spectrometry was performed by the Proteomics Facility of the University of Konstanz (Germany). The identification of retinin in non-*melanogaster* species was performed by Protein Analysis Facility of the University of Lausanne (Switzerland).

Atomic-force microscopy (AFM) For AFM, corneal samples prepared as described above were attached to a coverslip by a double-sided bonding tape. Microscopy was performed by the NTegra-Prima microscopes (NT-MDT, Zelenograd, Russia) using the contact and semi-contact procedure with the cantilever NSG 11 (NT-MDT) and JPK NanoWizard II (JPK, Berlin, Germany) with cantilever Tap300AI-G (Budget Sensors) in AC mode.

Retinin Purification and Generation of Polyclonal Rabbit Anti-Retinin Antibodies Truncated retinin sequence (SEQ ID NO:2), without the signal peptide-coding sequence (amino acids 1-21), was amplified from the pUASTattB-retinin plasmid with following primers: CTGTATACATATGAGAGGATCTCACCAT-CACCATCACCATGCCAGCTTGGAGTGGCCCTC (forward primer 2, SEQ ID NO:6), and CTGTTGACTCGAGCCTTAGTTGCGGATGAGAAC-CACTCG (reverse primer 2, SEQ ID NO:7). The forward primer encompasses the RGSHis-tag coding sequence, added to the N-terminus of retinin. The PCR product was subcloned into the NdeI and XhoI sites of pET23b and the resulting plasmid was transformed into the Rosetta-gami™ (Novagen) *E. coli* strain for recombinant expression upon induction by IPTG. The bacterial mass was lysed by French press (Constant Systems LTD). RGSHis-retinin protein was purified using the HisPur™ Ni-NTA resin (ThermoFisher scientific) following the manufacturer's recommendations and used to prepare polyclonal rabbit anti-retinin antiserum by Eurogentec S.A. (LIEGE Science Park, Seraing, Belgium). In Western blots, the anti-retinin antiserum was used at the 1:200 dilution. Antibodies to α-tubulin (GTX102079, Lucerna-chem) were used to probe for the loading control. In order to identify of RGSHis-tagged retinin in control experiment the antibodies to α-RGSHis-tag (QIAexpress, QIAGEN) were used.

Example 2: Identification of Retinin as Main Component in In Vitro Nanocoating

Samples from corneae and the retinae of wild-type adult *D. melanogaster* fruit flies were prepared separately. SDS-PAGE analysis identified major protein bands enriched in the cornea but not in the underlying retina of the fruit fly (FIG. 2*a,d*). Mass-spectrometry identified in these bands peptides corresponding to the following major proteins: Crystallin (Crys), Cuticular protein 72Ec (Cpr72Ec), and retinin. While retinin (predicted molecular weight (MW) =20.0 kDa) is the major protein found in the lower band migrating at ca. 25 kDa, peptides from Crys (predicted MW=55.9 kDa) and Cpr72Ec (predicted MW=50.6 kDa) provide the major signal in the other bands analyzed, suggesting extensive cross-linking of these proteins in corneae and partial degradation during sample preparation (FIG. 2*d*). Minor proteins identified in these samples correspond to certain metabolic enzymes, such as Alcohol dehydrogenase, Enolase, and Triose phosphate isomerase, as well as to proteins contaminating from the underlying retinal layer. While the presence of some metabolic enzymes on the surface of the eye may be an adaptation to the life style of *D. melanogaster*, which are fruit flies largely feeding on rotten and fermenting fruits, Crys (also known as Drosocrystallin), Cpr72Ec, and retinin are structural proteins.

In order to analyze the possible contribution of these corneal proteins to formation of nanocoatings, we used *Drosophila* genetics to specifically downregulate each of the proteins one by one in the insect's eyes using the GMR-Gal4 to drive respective UAS-RNAi constructs. AFM analysis of the mutant corneae reveals prominent defects in the nanostructures induced upon downregulation of retinin (FIG.

Figure 2I:
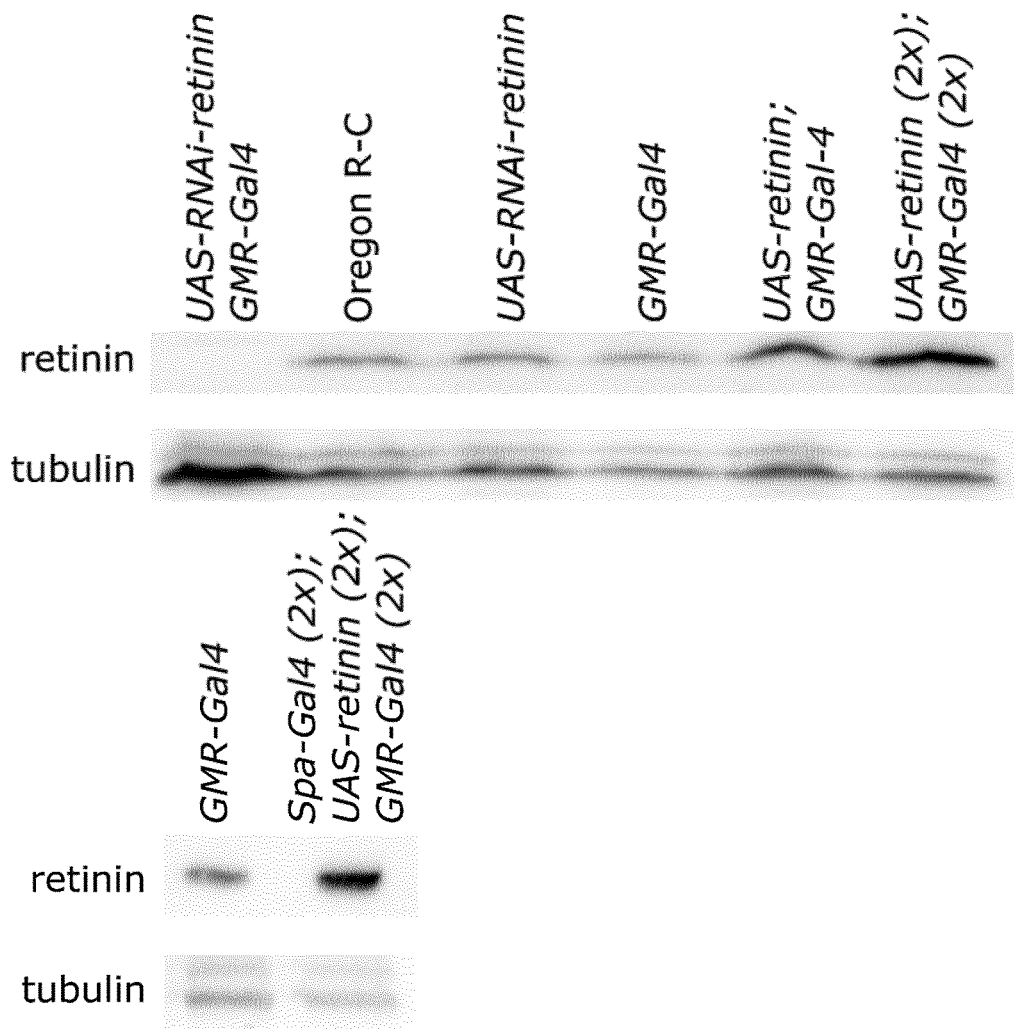
FIG. 2 shows identification of retinin as protein required for formation of corneal nanocoatings. (a) Scheme of separation of the eye material into retina (left, elongated) and cornea (right, rounded). (b, c) AFM analysis of wild-type Drosophila corneal surfaces before (b) and after detergent treatment (c). (d) SDS-PAGE of samples from retina and cornea. Major protein bands unique for cornea (marked by arrows) were identified by peptide mass-spectrometry. Positions of molecular weight standards are indicated to the left of the gel. (e) AFM analysis of RNAi-induced mutant cornea knocked-down for retinin. (f-h) Quantification of the characteristics of nipple nanostructures: the height (f), the diameter (g) and the square on the half-height (h) for wild type and different knocked-down phenotypes. Data are shown as mean±SD; n=50, different regions were analyzed. Statistical significance of the differences from the control wild-type genotype was assessed by Student test; "*" means p-value≤0.05; "" means p-value≤0.01; "*" means p-value≤0.001 "****" means p-value≤0.0001.

2e-h), while downregulation of Crys and Cpr72Ec resulted in milder phenotypes (FIG. 2f-h). To assess the degree of retinin downregulation, we generated antibodies against this protein and confirmed the strong drop in its levels upon eye-specific expression of the retinin-targeting RNAi construct (FIG. 2i).

Conclusion

Our data pinpoint retinin as a major protein component of insect corneal nanostructures, whose downregulation provokes severe defects in nanostructure formation.

Figure 3C:
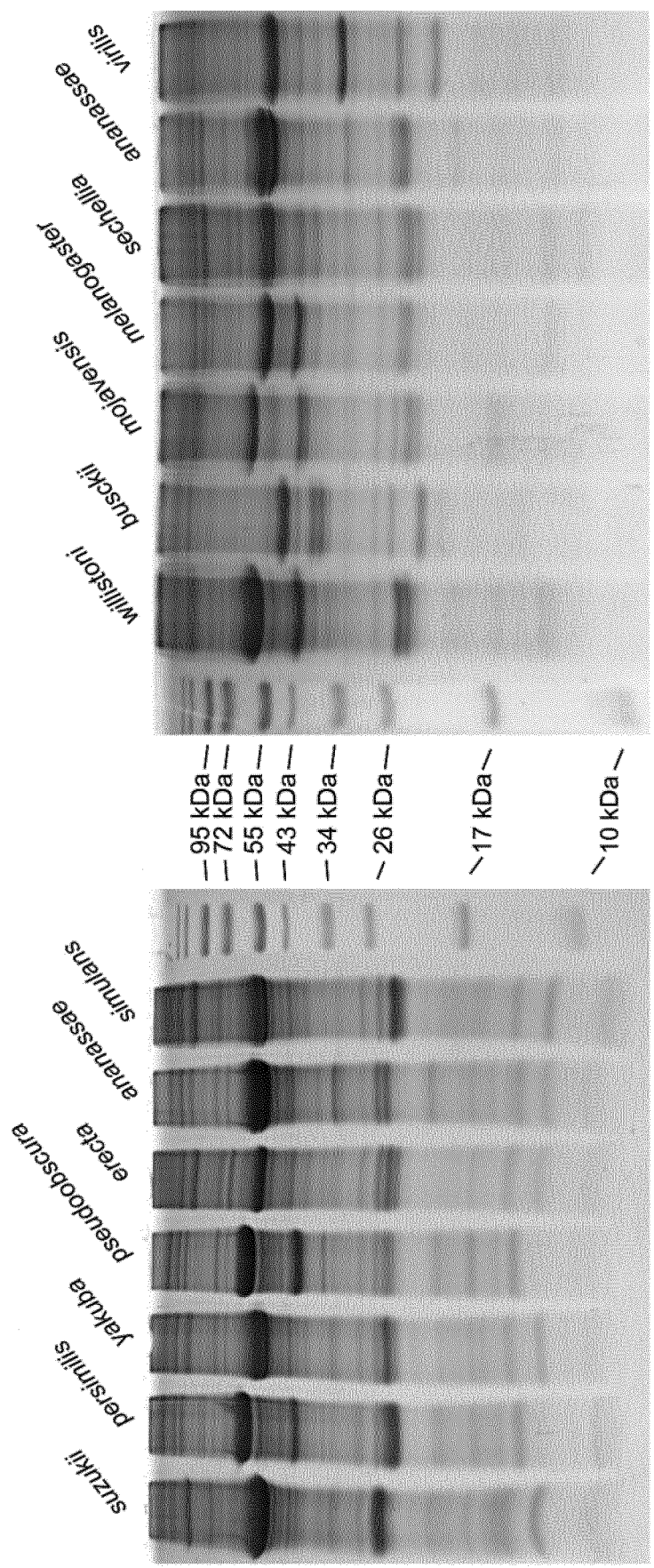

Example 3: Retinin Play a Central Role for Order and Patterning in Corneal Nanostructures in *Drosophila* Genus The role of retinin in formation of nanostructures was probed by correlating the protein expression levels with the corneal nanopatterns in different *Drosophila* species. Thus, to evaluate the importance of retinin, we performed proteomic characterization of corneae from 13 other *Drosophila* species, revealing that the protein composition was similar to that of *D. melanogaster* (FIG. 3c).

AFM analysis of corneal nanocoatings of the 14 species of the genus *Drosophila* revealed two principal types of nanocoatings to be present in this insect group: individual nipple-type nanostructures like in *D. melanogaster*, seen additionally in *D. virilis*, *D. busckii*, *D. erecta*, *D. simulans* *D. yakuba*, and *D. sechellia*, and partial fusions of such nanostructures into ridges, observed in *D. pseudoobscura*, *D. ananassae*, *D. persimilis*, *D. suzukii*, *D. grimshawi*, and *D. willistoni* (FIG. 3a-b). There was a strong correlation of the morphological type with the level of retinin expression in these species, as the nipple-to-ridge species possess significantly more retinin in their corneae than the nipple-only species (FIG. 3b). Additionally, there was correlation between retinin expression levels and the degree of order in the packing of individual nanostructures.

Conclusion

Experiments demonstrate that retinin plays an important role in formation of insect corneal nanostructures, not only in *D. melanogaster*, but also in the entire *Drosophila* genus. The data show that retinin levels influence the resulting nanopatterns, thereby supporting the notion that a diverse set of nanocoatings can be formed by varying the admixing procedure.

Example 4: Identification of Lipid as Main Component in In Vitro Nanocoating

To identify the potential second morphogen of the nanostructured patterns, the inventors targeted the wax biosynthetic pathway in *Drosophila* corneae.

Figure 4H:
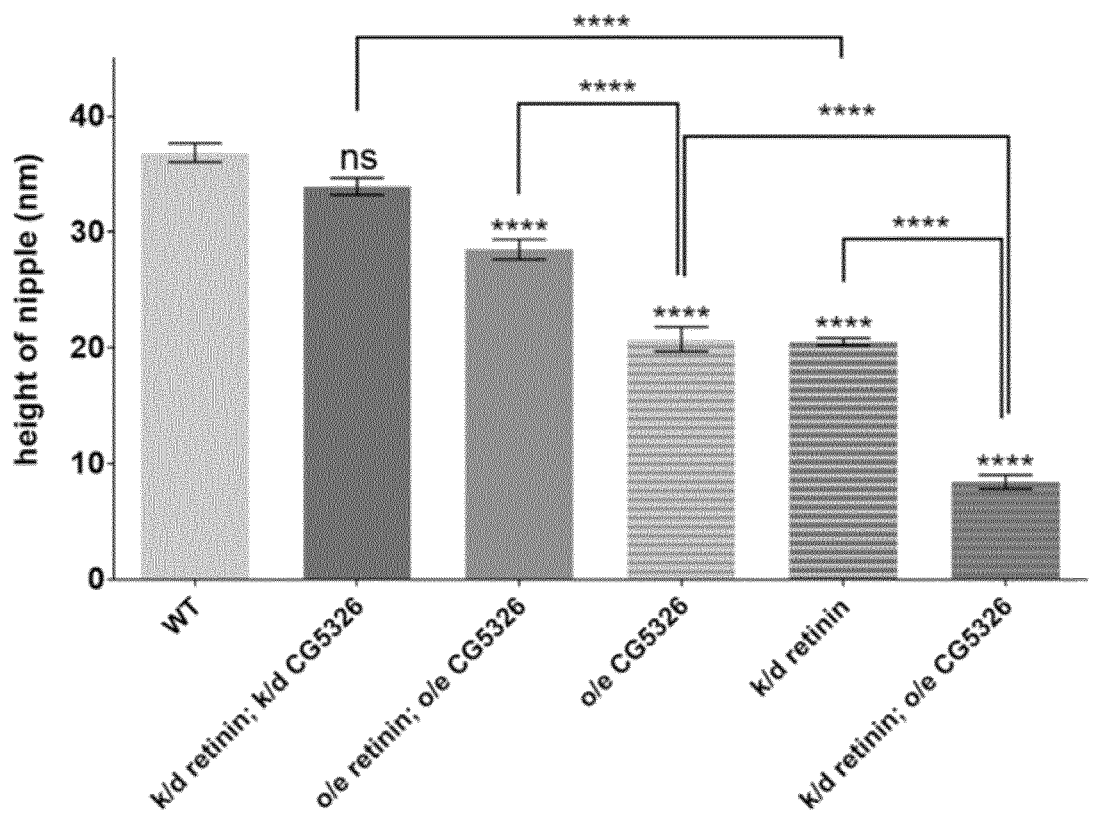

The wax biosynthesis pathway has not previously been characterized in the arthropods. Initially, *Drosophila* homologs of two enzymes in the mammalian wax synthesis pathway were probed, (i) elongase converting long-chain fatty acids into very long-chain fatty acids, and (ii) acyltransferase making long-chain ester waxes from long-chain acyl-CoA and long-chain alcohol (FIG. 4a). Six *Drosophila* homologs of elongase with significant level of expression in the head tissues or/and in the eyes in particular were identified; five non-characterized genes (CG2781, CG31523, CG31522, CG33110, CG5326) and the known (CG3971 Baldspot). RNAi-mediated downregulation of each of these genes in the eye using the GMR-Gal4 driver revealed that knockdown of CG5326, but not any of the other elongase homologs, induced fusion of individual nipples into ridges (FIG. 4b) just as retinin overexpression does. Reciprocally, overexpression of CG5326 by spa-Gal4 induced impressive nipple shrinkage (FIG. 4c), just as retinin knockdown does. The effect of nanostructure morphology is quantified in FIG. 4f-g and FIG. 4h. Thus, CG5326 functions as a *Drosophila* ortholog to the mammalian elongase, and evidently affects the formation of insect corneal nanostructures.

As for the second enzyme in the mammalian wax biosynthetic pathway, *Drosophila* CG1942 was identified as the only ortholog to the mammalian acyltransferase (long-chain-alcohol 0-fatty-acyltransferase AWAT1 and AWAT2). Remarkably, loss-of-function mutation of this non-characterized gene also induced nipple-to-ridge transformation (FIG. 4e), similarly to downregulation of CG5326 or overexpression of retinin.

Conclusion

The data shows that lipids can be designated as the second morphogen of the nanostructured patterns and at least plays an important role in the formation of insect corneal nanostructures.

Example 5: Formation of In Vitro Nanocoatings with Retinin and Different Lipids

The possibility to form in vitro nanocoatings was initially tested by a dot blot assay using recombinantly produced retinin or a similarly-sized unrelated protein Dhit as a control, on one hand, and a set of commercial waxes (lanolin, paraffin, beeswax and carnauba), on the other. To this end, a robust line of low-cost production of recombinant retinin from bacteria was established (see example 1). Recombinant retinin is produced as a clean soluble protein.

Waxes Emulsion Preparation 4 g of each wax (paraffin, beeswax, carnauba wax #1 (Aldrich chemistry) and lanolin (Sigma)) were added to different tubes with 40 ml 10% SDS solutions, and sonicated in a water bath (AL 04-04, Advantage-Lab) for 2 hours at a temperature of 80° C. After 24 hours of incubation at 25° C., the top part, enriched in wax nanodrops, was diluted in PBS solution by 10 times and incubated for 48 hours at 25° C. The upper part of this solution, enriched in the wax drops with the size bigger than 500 nm, was discarded. The lowest part was dissolved in PBS approximately by 10 times, until the optical density of the solution at a wavelength of 600 nm became 0.5 AE. These emulsions are stable at 25° C.

Identification of Specific Interaction of the Retinin Protein with Waxes

Drops with 3 µl of each wax emulsion were dried on nitrocellulose at 50° C., and blocked with 3.5% fat free milk powder solution in PBS overnight. After this step the nitrocellulose was cut into two parts, the first part was incubated with 3.5% fat free milk powder solution in PBS with retinin (1.2 µg/ml), the second part—with 3.5% fat free milk powder solution in PBS with Dhit protein (1.2 µg/ml) for 1 hour. Both parts were washed 3 times by PBS and blocked with 3.5% fat free milk powder solution in PBS for 1 hour. After this, the standard protocol for Western blot was used with antibodies to α-RGSHis-tag (QIAexpress, QIAGEN).

The dot blot assay demonstrate that the control protein, Dhit, has no capacity to interact with the waxes, while retinin binds them with strong efficiency (FIG. 5a) demonstrating a pronounced physical interaction.

To re-synthesize corneal nanostructures in vitro, recombinant retinin and commercial waxes were admixed. Surprisingly, layering the two components on glass surfaces formed ordered nanocoatings (FIG. 5d), while retinin alone (FIG. 5c) or wax alone (FIG. 5e) were inefficient. The observation that ordered nanocoatings could be formed by admixing retinin with a lipid was confirmed by admixing retinin with paraffin or bees wax (FIG. 5f). Additional examples of nanocoatings formed by a variety of lipids is given in FIG. 5g (from left to right: olive oil, lanolin wax, paraffin, beeswax, carnauba wax). Moreover, mixing BSA, a non-retinin-like molecule, with carnauba wax did not result in the formation of an ordered nanocoating (FIG. 5h, right) as compared to mixing retinin with carnauba wax (FIG. 5h, left).

An exemplary protocol permitting efficient formation of in vitro nanocoatings is as follows: A mixture containing 5 µl of the retinin solution (0.6 mg/ml) and 15 µl of carnauba wax emulsion (pH=9.0) is evenly distributed on a 1 cm$^2$ area of the cover slip glass and dried within 20 minutes (at 50-60% humidity), rinsed by water, and re-dried. Next, 20 µl of the retinin solution is evenly distributed on the pre-coated surface, dried, rinsed by water, and re-dried. The resulting nanocoating consisted of nanostructures of the typical dimensions of ca. 200 nm in width and 50 nm in height (FIG. 5d). These dimensions are similar to the original *Drosophila* corneal nanocoatings (FIG. 1).

Conclusion

The experiments demonstrates in vitro nanocoating formation is possible using only recombinant retinin and lipid.

Example 6: Functionality of In Vitro Nanocoatings

The nanocoatings were tested advantageous properties; in particular, reflectance and wettability were probed as described below.
Reflectance Measurements
Using the JASCO MSV-370 micro-spectrophotometer in the reflection geometry, non-dispersive Schwarzschild-objective and an aperture, the region of interest was set to an area of 300×300 µm. The spectral region from UV spectrum (300 nm) to near infrared (750 nm). The data is used to visualize the spectral ratio (R(of interest)/R(glass)) between the two samples.
Wettability Test
The measurement was performed using a digital camera. After a droplet of 5 µl of water was positioned upon the sample surface, the images were captured and analyzed with the Gwyddion software. The contact angles were measured from both sides of the droplet.

The in vitro nanocoatings possessed both anti-reflective function across the visual range (FIG. 6a), and anti-wetting function (FIG. 6b).

Conclusion

The experiments show that the in vitro nanocoatings possess advantageous properties, such as anti-reflection and anti-wetting, which can be applied to natural or artificial surfaces to provide them with new properties. Furthermore, the in vitro nanocoatings possess several additional advantages compared to other existing nanocoatings. This is schematically illustrated in FIG. 9.

Example 7: Testing of Parameters for Formation of In Vitro Nanocoating

To test the versatility of the method and the in vitro nanocoating protocol, parameters such as i) wax identity; ii) retinin/wax ratio; iii) incubation time prior to washing; iv) incubation temperature was varied (FIG. 7). 20 µl of mixed solution of retinin solution in TBS (0.6 mg/ml) and wax emulsion in different proportions (FIG. 7a-c) were evenly distributed on a 1 cm$^2$ area of the cover slip glass and dried for 20 minutes (50-60% humidity), washed in water, and re-dried. In some experiments the protocol was repeated twice (FIG. 7f, g, i-l), or 3 times (FIG. 7h), with (FIG. 7g-l), or without (FIG. 7f) the washing step in between. A mix of retinin solution and different wax emulsions—lanolin (i), beeswax (j), paraffin (k), or carnauba wax (l)—was used. All protocols produced re-synthesized in vitro nanocoatings (FIG. 7).

Conclusion

The experiments show that different protocols (e.g. different proportions, washing or not, 1, 2 or 3 times repetition or different waxes) may be used to form diverse correctly re-synthesized patterns useful for different applications.

Example 8: Formation of In Vitro Nanocoating from Mixing of Retinin and Olive Oil To verify that in vitro nanocoatings can be formed using a diverse set of lipid, nanocoatings comprising olive oil emulsion was produced (FIG. 8). Olive oil is mainly composed of a mix of triglyceride esters of a selection of fatty acids, which varies depending on cultivation, region, extraction method etc. The predominant fatty acid is oleic acid, with significant amounts of also linoleic acid and palmitic acid. Additional constituents of olive oil would be known to a person skilled in the art.

A mix of 15 µl of retinin solution (0.6 mg/ml) and 5 µl of olive oil emulsion (pH=9) was evenly distributed on a 1 cm$^2$ area of the cover slip glass and dried within 20 minutes (50-60% humidity), washed in water, and dried again. On the second step the same solution was evenly distributed on this surface, dried, washed in water, and re-dried. The process produced a re-synthesized in vitro nanocoating (FIG. 8).

Conclusion

The experiment shows that it is possible to form in vitro nanocoatings from a diverse set of lipids, here exemplified with olive oil.

Example 9: Formation of In Vitro Nanocoating from Further Proteins

To verify that in vitro nanocoatings can be formed using a diverse set of proteins, nanocoatings comprising CG13059 and CPR10 was produced (FIG. 10). CG 13059 is a protein found in *D. melanogaster* and CPR10 is a protein found in *A. gambiae* (FIG. 10a-b).

20 µl of mixed solution of protein solution in PBS (0.6 mg/ml) and lanolin emulsion in different proportions (3:17 for CG13059 and 1:1 for CPR10) were evenly distributed on 1 cm$^2$ area of the cover slip glass and dried for 20 minutes (50-60% humidity), washed in water, and redried. The process produced a re-synthesized in vitro nanocoating (FIG. 10d-e). The in vitro nanocoating produced from CPR10 and lanolin wax displayed reliable anti-reflective activity (FIG. 10c).

Conclusion

The experiment shows that it is possible to form in vitro nanocoatings from a diverse set of proteins including cuticular proteins, here exemplified with CG13059 and CPR10.

REFERENCES

US 2009/0231714 A1
Nanoscale, 2015,7, 5922-5946

The invention claimed is:

1. A method for preparing a coated surface, said method comprising:
   i. mixing a protein solution, which comprises retinin, retinin-like protein, or cuticular protein with an emulsion or suspension, which comprises one or more lipids so as to obtain a liquid mixture,
   ii. contacting a surface with said liquid mixture, and
   iii. drying said surface, thereby providing a coated surface.

2. The method according to claim 1, wherein the retinin, retinin-like protein, or cuticular protein is present in an insect belonging to the order *Diptera*.

3. The method according to claim 2, wherein the insect belongs to the genus *Drosophila*.

4. The method according to claim 3, wherein the insect is *D. melanogaster*.

5. The method according to claim 1, wherein the retinin, retinin-like protein, or cuticular protein is a recombinant retinin, recombinant retinin-like protein, or recombinant cuticular protein.

6. The method according to claim 1, wherein the protein solution comprises retinin or retinin-like protein.

7. The method according to claim 6, wherein the retinin or retinin-like protein comprises an amino acid sequence selected from:
   i. SEQ ID NO: 1, or
   ii. an amino acid sequence having at least 80% sequence identity to SEQ ID NO: 1.

8. The method according to claim 6, wherein the retinin or retinin-like protein comprises an amino acid sequence selected from:
   i. SEQ ID NO: 2, or
   ii. an amino acid sequence having at least 80% sequence identity to SEQ ID NO: 2.

9. The method according to claim 6, wherein the retinin or retinin-like protein comprises the amino acid sequence selected from:
   i. SEQ ID NO: 3, or
   ii. an amino acid sequence having at least 80% sequence identity to the SEQ ID NO: 3.

10. The method according to claim 1, wherein the one or more lipids are molecules comprising one or more carbon chains comprising at least 10 carbons atoms.

11. The method according to claim 1, wherein the one or more lipids comprise a wax.

12. The method according to claim 11, wherein the wax is selected from the group consisting of a carnauba wax, beeswax, paraffin wax, lanolin wax, Chinese wax, shellac wax, spermaceti, bayberry wax, candelilla wax, castor wax, esparto wax, Japan wax, ouricury wax, soy wax, tallow tree wax, ceresin waxes, montan wax, ozocerite, peat waxes, and microcrystalline wax, or any combinations thereof.

13. The method according to claim 6, wherein the retinin or retinin-like protein comprises the common Retinin C-domain designated PF04527 as described in the PFAM database of protein families, also known as Retinin-like domain designated IPR007614 as described in the InterPro database of proteins.

14. A method of making a coated product comprising:
   mixing a protein solution, which comprises retinin, retinin-like protein, or cuticular protein with an emulsion or suspension, which comprises one or more lipids so as to obtain a liquid mixture,
   contacting a surface of a contact lens, a glass-containing material, a display, a solar panel, a painting, a biological implant, or an electric wire with said liquid mixture, and
   drying said surface thereby making said coated product.

* * * * *

SEQUENCE LISTING

<160> NUMBER OF SEQ ID NOS: 9

<210> SEQ ID NO 1
<211> LENGTH: 67
<212> TYPE: PRT
<213> ORGANISM: Diptera
<220> FEATURE:
<221> NAME/KEY: Common Retinin C Domain
<222> LOCATION: (1)..(67)

<400> SEQUENCE: 1

Thr Ile Gln Glu Pro Ala Val Ala Lys Val Gly Glu Val Val Gln His
1               5                   10                  15

Val Pro Thr Ala Val Ser His Gln Thr Gln Thr Val Val His Asp His
            20                  25                  30

Arg Arg Leu Val Thr Pro Ile Val Ala Pro Ala Val Arg Thr Thr Gln
        35                  40                  45

Val Ile Arg Gln Gln Pro Pro Leu Leu Trp Ser Val Ala Ser Asp Pro
50                  55                  60

Arg Val Val
65

<210> SEQ ID NO 2
<211> LENGTH: 170
<212> TYPE: PRT
<213> ORGANISM: Drosophila melanogaster
<220> FEATURE:
<221> NAME/KEY: Retinin sequence without signal peptide
<222> LOCATION: (1)..(170)

<400> SEQUENCE: 2

Ala Ser Leu Glu Trp Pro Ser Asn Leu Val Ala Leu Ser Ser Val Lys
1               5                   10                  15

Ser Ser Gln Leu Leu Pro Ile Ala Ser Glu Asp Ser Val Glu Leu Ala
            20                  25                  30

Asp Gly Ser Ser Gly Ser Val Ser Ser Ala Ala Gln Pro Glu Asp
        35                  40                  45

Gln Ser Gln Glu Glu Ala Glu Glu Gln Gln Val Ser Ser Ala Ser Ser
50                  55                  60

Gly Ser Ala Asp Pro Ile Ser Gly Arg Leu Val Ser Ala Gly Ile Pro
65                  70                  75                  80

Val Ser Val Pro Leu Pro Leu Ile Leu Ala Ala Arg Asn Gly Leu Arg
            85                  90                  95

Thr Val Leu Thr Ile Gln Glu Pro Ala Val Ala Lys Val Gly Glu Val
        100                 105                 110

Val Gln His Val Pro Thr Ala Val Ser His Gln Thr Gln Thr Val Val
        115                 120                 125

His Asp His Arg Arg Leu Val Thr Pro Ile Val Ala Pro Ala Val Arg
130                 135                 140

Thr Thr Gln Val Ile Arg Gln Gln Pro Pro Leu Leu Trp Ser Val Ala
145                 150                 155                 160

Ser Asp Pro Arg Val Val Leu Ile Arg Asn
            165                 170

<210> SEQ ID NO 3
<211> LENGTH: 191
<212> TYPE: PRT
<213> ORGANISM: Drosophila melanogaster
<220> FEATURE:
<221> NAME/KEY: Full length retinin sequence

<222> LOCATION: (1)..(191)

<400> SEQUENCE: 3

Met Ser Arg Leu Phe Leu Pro Val Leu Ala Ile Val Leu Val Ser Ile
1               5                   10                  15

Gly Ala Ser His Thr Ala Ser Leu Glu Trp Pro Ser Asn Leu Val Ala
            20                  25                  30

Leu Ser Ser Val Lys Ser Ser Gln Leu Leu Pro Ile Ala Ser Glu Asp
        35                  40                  45

Ser Val Glu Leu Ala Asp Gly Ser Ser Gly Ser Val Ser Ser Ser Ala
    50                  55                  60

Ala Gln Pro Glu Asp Gln Ser Gln Glu Ala Glu Glu Gln Val
65                  70                  75                  80

Ser Ser Ala Ser Ser Gly Ser Ala Asp Pro Ile Ser Gly Arg Leu Val
                85                  90                  95

Ser Ala Gly Ile Pro Val Ser Val Pro Leu Pro Leu Ile Leu Ala Ala
            100                 105                 110

Arg Asn Gly Leu Arg Thr Val Leu Thr Ile Gln Glu Pro Ala Val Ala
        115                 120                 125

Lys Val Gly Glu Val Val Gln His Val Pro Thr Ala Val Ser His Gln
130                 135                 140

Thr Gln Thr Val Val His Asp His Arg Arg Leu Val Thr Pro Ile Val
145                 150                 155                 160

Ala Pro Ala Val Arg Thr Thr Gln Val Ile Arg Gln Pro Pro Leu
                165                 170                 175

Leu Trp Ser Val Ala Ser Asp Pro Arg Val Val Leu Ile Arg Asn
            180                 185                 190

<210> SEQ ID NO 4
<211> LENGTH: 18
<212> TYPE: DNA
<213> ORGANISM: Artificial sequence
<220> FEATURE:
<223> OTHER INFORMATION: Forward primer 1

<400> SEQUENCE: 4
gtaaccagca accaagta                                                 18

<210> SEQ ID NO 5
<211> LENGTH: 18
<212> TYPE: DNA
<213> ORGANISM: Artificial sequence
<220> FEATURE:
<223> OTHER INFORMATION: Reverse primer 1

<400> SEQUENCE: 5
gtccaattat gtcacacc                                                 18

<210> SEQ ID NO 6
<211> LENGTH: 60
<212> TYPE: DNA
<213> ORGANISM: Artificial sequence
<220> FEATURE:
<223> OTHER INFORMATION: Forward primer 2

<400> SEQUENCE: 6
ctgtatacat atgagaggat ctcaccatca ccatcaccat gccagcttgg agtggccctc   60

<210> SEQ ID NO 7
<211> LENGTH: 39

<212> TYPE: DNA
<213> ORGANISM: Artificial sequence
<220> FEATURE:
<223> OTHER INFORMATION: Reverse primer 2

<400> SEQUENCE: 7
ctgttgactc gagccttagt tgcggatgag aaccactcg                              39

<210> SEQ ID NO 8
<211> LENGTH: 200
<212> TYPE: PRT
<213> ORGANISM: Anopheles gambiae
<220> FEATURE:
<221> NAME/KEY: CPR10 protein
<222> LOCATION: (1)..(200)

<400> SEQUENCE: 8

Met Ala Ser Lys Ile Ser Leu Ile Ala Val Gly Leu Leu Val Asn
1               5                   10                  15

Val Gly Val Asn Ala Gln Gln Tyr Gly Gln Gln Leu Gly Arg Arg Ser
            20                  25                  30

Ser Gln Asp Arg Leu Asn Gln Leu Arg Ser Tyr Asp Asp Gly Ala Arg
        35                  40                  45

Gln Ser Arg Asn Tyr Asn Asp Leu Tyr Asn Glu Gln Arg Tyr Ala Ser
    50                  55                  60

Arg Thr Gln Asp Gln Glu Gln Gln Gln Gln Gln His Gln Asp Arg
65                  70                  75                  80

Arg Glu Ser Ser Asp Tyr Asp Arg Asp Tyr Ser Tyr Gly Tyr Ala
                85                  90                  95

Val Arg Asp Glu Leu Ser Gly Asp Ile Lys Ser Gln Gln Glu Val Arg
            100                 105                 110

Asn Gly Asp Arg Val Arg Gly Gln Tyr Arg Thr Leu Glu Ser Asp Gly
        115                 120                 125

Thr Glu Arg Ile Val Asp Tyr Thr Ala Asp Asp Val Arg Gly Phe Asn
    130                 135                 140

Ala Val Val Arg His Gln Pro Ser Val Gly Thr Arg Ala Gln Leu Val
145                 150                 155                 160

His Thr Leu Gln Pro Ala Val Leu Leu Arg Gln Pro Thr Val Gly His
                165                 170                 175

Leu Val Ser Gly Gln His Arg Pro Ala Leu Leu Thr Thr Pro Gln Gln
            180                 185                 190

Thr Ser Thr Val Leu Leu Arg Asn
        195                 200

<210> SEQ ID NO 9
<211> LENGTH: 155
<212> TYPE: PRT
<213> ORGANISM: Drosophila melanogaster
<220> FEATURE:
<221> NAME/KEY: CG13059 protein
<222> LOCATION: (1)..(155)

<400> SEQUENCE: 9

Met Phe Lys Phe Val Ala Phe Phe Ala Cys Leu Ala Val Ala Ala
1               5                   10                  15

Ala Pro Gly Leu Ile Ala Glu Thr His Ser Ile Val Gln Pro Ala Ile
            20                  25                  30

Leu Ala Lys Thr Ala Tyr Val Asp Thr Ser Ala Ser Ser Ala Ile Thr
        35                  40                  45

-continued

```
His Gln Ser Asn Val Asn Leu Val Arg Lys Val Pro Val Val Tyr Ser
    50                  55                  60

Ala Pro Val Val His Ala Ala Pro Val Val His Ala Ala Pro Leu Val
65              70                  75                  80

Lys Thr Val Ile Pro Ala Ala Pro Leu Val Lys Thr Val Ile Pro Ala
                85                  90                  95

Ala Pro Val Leu Lys Thr Val Val Ser Ser Ala Pro Leu Val His Thr
                100                 105                 110

Val Val Pro Ala Ala Pro Leu Val Lys Thr Val Ile Pro Ala Ala Pro
            115                 120                 125

Val Ile Lys Thr Val Ile Pro Ala Ala Pro Leu Val His Thr Val His
        130                 135                 140

Ser Ala Pro Val Val Tyr Ser Ala Tyr His Lys
145                 150                 155
```